(12) United States Patent
Katayama et al.

(10) Patent No.: US 7,427,640 B1
(45) Date of Patent: Sep. 23, 2008

(54) OIL MATERIALS COMPRISING DIMERDIOL ESTER AND COSMETICS COMPRISING THE ESTER

(75) Inventors: Tsuyoshi Katayama, Takasago (JP);
Masakazu Okumura, Takasago (JP);
Nobuaki Hattori, Takasago (JP);
Makoto Nakajima, Takasago (JP);
Osamu Kimura, Takasago (JP)

(73) Assignee: Nippon Fine Chemical Co., Ltd., Osaka (JP)

( * ) Notice: Subject to any disclaimer, the term of this patent is extended or adjusted under 35 U.S.C. 154(b) by 1412 days.

(21) Appl. No.: 09/604,763

(22) Filed: Jun. 26, 2000

(30) Foreign Application Priority Data

Jun. 28, 1999 (JP) ................................ 11-181497

(51) Int. Cl.
*A61K 47/14* (2006.01)
*A61K 8/00* (2006.01)
*A61K 8/02* (2006.01)

(52) U.S. Cl. .................... 514/785; 424/401; 424/64; 424/70.7; 424/59

(58) Field of Classification Search ................ 424/401, 424/78.03, 64, 70.7, 59; 514/785, 845, 937, 514/938, 943
See application file for complete search history.

(56) References Cited

U.S. PATENT DOCUMENTS

| | | | | |
|---|---|---|---|---|
| 3,846,550 A | * | 11/1974 | Akrongold et al. | ............ 424/63 |
| 4,788,054 A | * | 11/1988 | Bernhardt et al. | ............ 424/59 |
| 5,652,263 A | * | 7/1997 | Clum et al. | .................. 514/529 |
| 5,739,190 A | * | 4/1998 | Hartmann et al. | ........... 524/310 |
| 5,795,978 A | * | 8/1998 | Ansmann et al. | ............ 536/120 |
| 5,798,434 A | * | 8/1998 | Kigawa et al. | .............. 528/306 |
| 6,160,144 A | | 12/2000 | Bongardt et al. | |

FOREIGN PATENT DOCUMENTS

| | | |
|---|---|---|
| DE | 1289620 B | 2/1969 |
| WO | WO 9618598 | 6/1996 |

OTHER PUBLICATIONS

Database WPI Section Ch, Week 8344, Derwent Publications Ltd., London GB; XP002216838 and JP 58 162661 A (Sep. 27, 1983).

* cited by examiner

*Primary Examiner*—Sreeni Padmanabhan
*Assistant Examiner*—Gina C. Yu
(74) *Attorney, Agent, or Firm*—Birch, Stewart, Kolasch & Birch, LLP

(57) ABSTRACT

An oil material comprising a dimerdiol ester with a monocarboxylic acid having 4 to 34 carbon atoms or with a dimerdiol ester with a dicarboxylic acid; and a cosmetic and an external agent excellent in safety, stability, gloss, feeling and the like comprising the dimerdiol carboxylate.

14 Claims, No Drawings

OIL MATERIALS COMPRISING DIMERDIOL ESTER AND COSMETICS COMPRISING THE ESTER

BACKGROUND OF THE INVENTION

The present invention relates to oil materials comprising an ester of dimerdiol with monocarboxylic acid having 4 to 34 carbon atoms or an ester of dimerdiol with dicarboxylic acid, and cosmetics and external agents comprising the dimerdiol ester. More specifically, the present invention relates to oil materials comprising a dimerdiol carboxylate excellent in safety, stability, gloss, feeling and the like, and cosmetics and external agents comprising the ester excellent in safety, stability, gloss, feeling and the like. (Hereinafter, "ester of dimerdiol" is referred to as "dimerdiol ester".)

DESCRIPTION OF THE RELATED ART

Conventionally, various esters and oil materials comprising the esters have been used in cosmetics and external agents. For example, cetyl isooctanoate, isodecyl isononanoate, isopropyl palmitate, octyldodecyl myristate, octyl stearate, isostearyl isostearate, glyceryl isooctanoate, glyceryl isostearate, octyldodecyl oleate, ethyl linoleate, ethyl cinnamate, octyl salicylate, propyl p-oxybenzoate, dioctyl phthalate, diisostearyl malate and the like are known. However, these esters are not necessarily satisfactory in safety, stability, gloss, feeling and the like as raw materials of cosmetics and external agents. Therefore, there have been a desire for raw materials of cosmetics excellent in safety, stability, gloss and feeling and further excellent in hydrolysis resistance, pigment dispersing property, less odor and the like.

The present inventors have intensively studied to solve the above-mentioned problems. As a result, they have found that a dimerdiol ester with a monocarboxylic acid having 4 to 34 carbon atoms, a dimerdiol ester with a dicarboxylic acid and oil materials comprising the ester are excellent in safety, stability, gloss, feeling of use and the like as a raw material of cosmetics and external agents. Thus, the present invention was completed.

SUMMARY OF THE INVENTION

The present invention provides an oil material comprising a dimerdiol ester with a monocarboxylic acid having 4 to 34 carbon atoms or a dimerdiol ester with a dicarboxylic acid.

The present invention further provides a cosmetic and an external agent excellent in safety, stability, gloss, feeling and the like comprising the dimerdiol carboxylate.

DETAILED DESCRIPTION OF THE PREFERRED EMBODIMENTS

The dimerdiols and/or esters thereof used for producing the dimerdiol carboxylate and oils comprising the ester of the present invention are known, and can be produced, for example, by hydrogen reduction of industrially obtainable dimer acids and/or esters thereof.

A dimer acid is a known dibasic acid obtainable by an intermolecular polymerization reaction of an unsaturated fatty acid, and the industrial production process thereof is approximately standardized in the art. For example, a dimer acid and/or a lower alcohol ester thereof can be obtained by dimerization of an unsaturated fatty acid having 11 to 22 carbon atoms and/or a lower alcohol ester thereof with a clay catalyst.

An industrially obtainable dimer acid is mainly composed of a dibasic acid having about 36 carbon atoms. It also contains a trimer acid and monomer acid in any amount depending on the degree of purification. In general, those in which the content of a dimer acid is over 70 wt % and those in which the content of a dimer acid has been increased to 90% or more are commercially available. Further, those which oxidation stability has been improved by hydrogenation of double bonds remaining after the dimerization reaction are also commercially available. In the present invention, any of dimer acids thus commercially available in present can be used.

An industrially obtainable dimerdiol contains other component, for example, a trimer triol, monoalcohol, and ether compound, depending on the degree of purification of a dimer acid and/or a lower alcohol ester there of used as a raw material. In general, those in which the content of a dimerdiol is over 70 wt % can be used in the present invention, although a high purity dimerdiol, such as a dimerdiol in which its content is over 90 wt %, is preferable.

A dimerdiol produced by hydrogenating a dimer acid obtained by dimerization of an unsaturated fatty acid having 11 to 22 carbon atoms with a clay catalyst usually contains 70 to 100 wt % of a diol component. It is considered that the dimerdiol mainly contains compounds represented by the following structural formula 1 and/or structural formula 2:

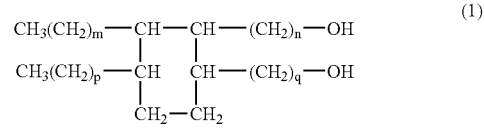

wherein, each of m, n, p and q independently represents an integer and m+n+p+q is from 14 to 36;

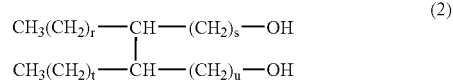

wherein, each of r, s, t and u independently represents an integer and r+s+t+u is from 18 to 40.

The monocarboxylic acid used in the present invention is not particularly restricted providing it has 4 to 34 carbon atoms, preferably 10 to 32 carbon atoms. Examples of the monocarboxylic acid used in the present invention include linear saturated acids such as butanoic acid, pentanoic acid, hexanoic acid, heptanoic acid, octanoic acid, nonanoic acid, decanoic acid, undecanoic acid, dodecanoic acid, tridecanoic acid, tetradecanoic acid, heptadecanoic acid, hexadecanoic acid, pentadecanoic acid, octadecanoic acid, nonadecanoic acid, eicosanoic acid, docosanoic acid, tetracosanoic acid and the like; branched fatty acids such as isobutanoic acid, isopentanoic acid, pivalic acid, isohexanoic acid, isoheptanoic acid, isooctanoic acid, diemthyloctanoic acid, isononanoic acid, isodecanoic acid, isoundecanoic acid, isododecanoic acid, isotridecanoic acid, isotetradecanoic acid, isopentadecanoic acid, isohexadecanoic acid, isoheptadecanoic acid, isooctadecanoic acid, isononadecanoic acid, isoeicosanoic acid, 2-ethylhexanoic acid, 2-butyloctanoic acid, 2-hexyldecanoic acid, 2-octyldodecanoic acid, 2-decyltetradecanoic acid, 2-dodecylhexadecanoic acid, 2-tetradecyloctadecanoic acid, 2-hexadecyloctadecanoic acid, long chain fatty acids obtained from lanolin, and the like; linear unsaturated fatty acids having 8-34 carbon atoms such as undecenoic acid, linderic acid, myristoleic acid, palmitoleic acid, oleic acid, linoleic acid, linolenic acid, elaidinic acid, gadolenoic acid, eicosapentaenoic acid, docosahexaenoic acid, erucic acid, brassidic acid, arachidonic acid and the like; hydroxy acids such as 2-hydrbxybutanoic acid, 2-hydroxypentanoic acid, 2-hydroxyhexanoic acid, 2-hydroxyheptanoic acid, 2-hydroxyoctanoic acid, 2-hydroxynonanoic acid, 2-hydroxydecanoic acid, 2-hydroxyundecanoic acid, 2-hydroxydodecanoic acid, 2-hydroxytridecanoic acid, 2-hydroxytetradecanoic acid, 2-hydroxyhexadecanoic acid, 2-hydroxyheptadecanoic acid, 2-hydroxyoctadecanoic acid, 12-hydroxyoctadecanoic acid, 2-hydroxynonadecanoic acid, 2-hydroxyeicosanoic acid, 2-hydroxydocosanoic acid, 2-hydroxytetracosanoic acid; long chain 2-hydroxy branched fatty acids obtained from lanolin and the like; cyclic acids such as cyclohesanoic acid, hydrogenated rosin, rosin, abietic acid, hydrogenated abietic acid, benzoic acid, p-oxybenzoic acid, p-aminobenzoic acid, cinnamic acid, p-methoxycinnamic acid, salicylic acid, gallic acid, pyrrolidonecarboxylic acid, nicotinic acid and the like. Further, naturally-derived fatty acids such as orange oil fatty acid, avocado oil fatty acid, macadamia nut oil fatty acid, olive oil fatty acid, hydrogenated soy bean oil fatty acid, jojoba oil fatty acid, palm oil fatty acid, hydrogenated palm oil fatty acid, palm kernel oil fatty acid, castor oil fatty acid, wheat germ oil fatty acid, safflower oil fatty acid, turtle oil fatty acid, cotton seed oil fatty acid, beef tallow fatty acid, hydrogenated beef tallow fatty acid, lanolin fatty acid, mink oil fatty acid and the like can also be used in the present invention since they contain a monocarboxylic acid having 4 to 34 carbon atoms.

The dicarboxylic acid used in the present invention is not particularly restricted providing it has two or more carboxyl groups in the molecule. Preferable are those represented by the following structural formula 3:

$$\text{HOOC}-(\text{CH}_2)_n-\text{COOH} \quad (3)$$

wherein, n is an integer from 1 to 16, more preferably from 3 to 16.

Examples of the dicarboxylic acid used in the present invention include malonic acid, succinic acid, glutaric acid, adipic acid, pimelic acid, suberic acid, azelaic acid, sebacic acid, 1,9-nonamethylenedicarboxylic acid, 1,10-decamethylenedicarboxylic acid, 1-, 1,1-undecamethylenedicarboxylic acid, 1-, 12-dodecamethylenedicarboxylic acid, 1-13-tridecamethylenedicarboxylic acid, 1-, 14-tetradecamethylenedicarboxylic acid, 1-,15-hexadecamethylenedicarboxylic acid.

In addition, above described dimer acid usable as a raw material of the dimerdiol can also be used as the dicarboxylic acid to be esterified with the dimerdiol.

The dimerdiol carboxylate of the present invention is obtained, for example, by esterification of a dimerdiol obtained as described above or transesterification of a lower alcohol ester thereof with a monocarboxylic acid having 4 to 34 carbon atoms described above or a dicarboxylic acid described above.

The esterification conditions are not particularly restricted. In general, the esterification is conducted by a conventional method.

For example, the esterification can be conducted by using, as a catalyst, p-toluenesulfonic acid, sulfuric acid, hydrochloric acid, methanesulfonic acid, boron trifluoride, hydrogen fluoride and the like, and using, as a solvent, benzene, toluene, hexane, heptane and the like, at 50 to 260° C. Alternatively, the esterification can be conducted with using neither solvent nor catalyst at 100 to 260° C.

In the transesterification reaction, an alkali catalyst such as sodium hydroxide, potassium hydroxide, potassium carbonate or the like, or a metal alkoxide such as sodium methoxide, sodium ethoxide, potassium butoxide or the like can be used as a catalyst.

In an esterification reaction with a monocarboxylic acid, the average esterification degree of the resulting ester can be arbitrarily controlled from monoester to diester by changing the charging ratio of a dimerdiol to a monocarboxylic acid.

The resulting ester may be a diester, a monoester or a mixture thereof depending on its use. The ester may be a mixture of two or more kinds of esters with different carboxylic acids. The oil materials of the present invention further comprises, in addition to the above esters, an ester with lower monocarboxylic acid such as acetic acid and propionic acid and/or an ester with a monocarboxylic acid having 34 or more carbon atoms. The oil materials of the present invention comprising the dimerdiol monocarboxylate thus obtained can be used in suitable uses as it is. Alternatively, it can be purified by a usual method, if necessary, before being applied to various used.

In an esterification reaction with a dicarboxylilc acid, the average esterification degree and the average molecular weight of the resulting ester can be controlled by changing the charging ratio of a dimerdiol to a dicarboxylic acid.

The charging ratio is preferably from 0.2 to 1.2 mol, more preferably from 0.4 to 1.0, in terms of the molar amount of a dicarboxylic acid based on the average molecular weight calculated from its acid value per 1 mol of a dimerdiol based on the average molecular weight calculated from its hydroxyl value.

The resulting dimerdiol dicarboxylate can have various average esterification degree and average molecular weight, and may be a mixed ester of two or more carboxylic acids, depending on its use. The oil materials of the present invention comprising a dimerdiol dicarboxylate thus obtained can be used in suitable uses as it is. Alternatively, it can be purified by a usual method, if necessary, before being applied to various use.

The dimerdiol monocarboxylate and dimerdiol dicarboxylate obtained as described above and oil materials comprising the ester are good in oxidation stability. The oxidation stability can be further improved by adding an antioxidant. As the antioxidant, those usually added to an oil material can be used, and particularly, vitamin E is desirable. As vitamin E, d-α-tocopherol, d-δ-tocopherol, d,1-α-tocopherol, d-α-tocopherol acetate, d,1-α-tocopherol acetate, tocopherol mixtures separated and purified from soy bean and rapeseed and the like can be used. The addition amount of the antioxidant is not particularly restricted, and suitably from 10 ppm to 10000 ppm based on the amount of ester.

In the esterification with a monocarboxylic acid, esters having a relatively high molecular weight from about 1,000 to 1,300 can be obtained. In spite of the relatively high molecular weight, the oil material has lower viscosity and manifests dry feeling without stickiness, causes little skin irritation and has high durability. Further, it has excellent oxidation stability and hydrolysis-resistance, and shows high refractive index and excellent gloss. Further, cosmetics and external agents comprising such a dimerdiol monocarboxylate are excellent in safety, hydrolysis-resistance, gloss and feeling of use.

In the esterification reaction with a dicarboxylic acid, a dimerdiol dicarboxylate can be obtained in which the weight-average molecular weight by GPC (gel permeation chromatography) analysis is from about 2,000 to 20,000. Particularly, when this weight-average molecular weight is from 4,000 to 12,000, it has excellent feeling of use in spite of the relatively high molecular weight and causes little irritation. Further, it has excellent oxidation stability, shows high refractive index and reveals excellent gloss. Still further, cosmetics and external agents containing such a dimerdiol dicarboxylate are excellent in safety, stability, pigment dispersability, gloss and feeling of use.

Content of the above dimerdiol ester with a monocarboxylic acid having 4 to 34 carbon atoms or a dimerdiol ester with a dicarboxylic acid in the oil material of the present invention is not particularly restricted, although, as a raw material for cosmetics, it is preferably 20% or more, and more preferably 50% or more.

Compounding amount of the dimerdiol ester comprised in the oil material of the present invention to cosmetics and external agents is not particularly restricted. Preferably, it is from about 0.1 to 50 wt %, particularly preferably from 0.5 to 30 wt %.

In the cosmetics of the present invention, water, and additives usually compounded into cosmetics such as fats and oils, emulsifier, alcohols, humectant, thickening agent, antioxidant, preservative, bactericide, chelating agent, pH regulator, ultraviolet absorber, opacifier, solvent, keratin ablation and resolution agent, antipruritic, antiphlogistine, antiperspirant agent, refrigerant, reductant, antihistamic agent, astringent, stimulant, hair growth agent, polymer powder, hydroxy acid, vitamins and derivatives thereof, saccharides and derivatives thereof, organic acids, enzymes, nucleic acids, hormones, clay minerals, aromatic, coloring agents and the like can be compounded, if necessary.

Examples of the fats and oils include higher alcohols such as cetanol, myristyl alcohol, oleyl alcohol, lauryl alcohol, cetostearyl alcohol, stearyl alcohol, arakyl alcohol, jojoba alcohol, chimyl alcohol, batyl alcohol, hexyl alcohol, isostearyl alcohol, 2-octyldodecanol and the like; lanolins such as liquid lanolin, reduced lanolin, adsorbed purified lanolin, lanolin acetate, liquid lanolin acetate, hydroxy lanolin, polyoxyethylene lanolin, lanolin fatty acid, hard lanolin fatty acid, lanolin alcohol, lanolin alcohol acetate, acetate and the like; phospholipids such as phosphatidyl choline, phosphatidyl ethanolamine, phosphatidyl inositol, sphingomyelin, phosphatidic acid, lysolecithine and the like; phospholipid derivatives such as hydrogenated soy bean phospholipid, hydrogenated yolk phospholipid and the like; sterols such as cholesterol, dihydrocholesterol, lanosterol, dihydrolanosterol, phytosterol and the like; sterol esters such as cholesteryl acetate, cholesteryl nonanoate, cholesteryl stearate, cholesteryl isostearate, cholesteryl oleate, di(cholesteryl behenyl octyldodecyl) N-lauroyl-L-glutamate, di(cholesteryl.octyldodecyl) N-lauroyl-L-glutamate, di(phytosteryl.2-octyldodecyl) N-lauroyl-L-glutamate, cholesteryl 12-hydroxystearate, cholesteryl macademia nut oil fatty acid ester, phytosteryl macademia nut oil fatty acid ester, phytosteryl isostearate, cholesteryl soft lanolin fatty acid ester, cholesteryl hard lanolin fatty acid ester, cholesteryl long chain branched fatty acid ester, chlesteryl long chain á-hydroxy fatty acid ester and the like; lower alcohol fatty acid esters such as ethyl oleate, ethyl avocado oil fatty acid ester, isopropyl palmitate, octyl paltitate, isopropyl isostearate, isotridecyl isononanoate, isopropyl lanolin fatty acid ester and the like; higher alcohol fatty acid esters such as octyldodecyl myristate, cetyl octanoate, oleyl oleate, octyldodecyl oleate, octyldodecyl lanolin fatty acid ester, hexyldecyl dimethyloctanoate, dioctyl succinate and the like; higher alcohol oxy acid esters such as cetyl lactate, diisostearyl malate and the like; polyhydric alcohol fatty acid esters such as trioleic glyceride, triisostearic glyceride, tri(capryl.capronic acid) glyceride, dioleic propylene glycol and the like; silicon resin; dimethicones such as methylpolysiloxane, octamethyltrisiloxane, decamethyltetrasiloxane, higher polymerized methylpolysiloxane and the like; phenyltrimethicones such as methylphenylpolysiloxane and the like; methicones such as methylhydrogenpolysiloxane and the like; organic modified polysiloxanes such as laurylmethicone copolyol, dimethiconol stearate, dimethicone copolyol isostearate and the like; amino modified polysiloxanes such as amodimethicone, amodimethicone copolyol and the like; crosslinked type methylpolysiloxanes such as crosslinked type methylphenyl polysiloxane, dimethicone/vinyldimethicone cross polymer and the like; anion modified polysiloxanes such as dimethicone copolyol phosphate, dimethicone copolyol sulfate and the like; alkylfluorodimethicones such as perfluoroethyl-stearyldimethicone and the like; perfluoro polyether and the like.

Examples of the emulsified include anionic surfactants such as fatty acid salts, alkylsulfate salts, alkylbenzenesulfonate salts, polyoxyethylenealkylsulfates salts, polyoxyethylene fatty amine sulfate salt, acyl N-methyltauric acid, alkylether phosphate salt, N-acylamino acid salt and the like; nonionic surfactants such as polyoxyethylene alkyl ether, polyoxyethylene alkylphenyl ether, polyoxyethylene alkyl ether sorbitan fatty acid parital ester, polyhydric alcohol fatty acid partial ester, polyglycerin fatty acid ester, polyoxyethylene fatty acid ester, alkyldimethylamine oxide, alkyl polyglycoside and the like; cationic surfactants such as alkyltrimethylammonium chloride, short chain polyoxyethylene alkylamine and salts and quaternary salts thereof, benzalconium chloride and the like; amphoteric surfactants such as alkyldimethylaminoacetic acid betaine, alkylamidedimethylaminoacetic acid betaine, 2-alkyl-N-carboxyl-N-hydroxyimidazolinium betaine and the like; polymer surfactants such as polyvinyl alcohol, sodium alginate, starch derivatives, gum tragacanth, acrylic acid methacryllic acid copolymer and the like.

Examples of the humectant include polyhydric alcohols such as propylene glycol, glycerin, 3-methyl-1,3-butane diol and the like; sodium hyaluronate, citrate salt, urea, lactic acid bacteria culture liqour, yeast extract, egg shell membrane protein, bovine submaxillary salivary gland mucin, hypotaurin, sesame lignan glucoside, betaine, chondroitin sulfate, ceramide (type 1, 2, 3, 4, 5, 6), hydroxyceramide, psuedoceramide, sphingoglucolipid, glutathione, polyethylene glycol, sorbitol, carbitol, sodium lactate, sodium 2-pyrrolidone-5-carboxylate, albumin, trimethylglycine; proteinolyzed peptide and derivatives thereof such as collagen, elastin, collagenolyzed peptide, elastinolyzed peptide, keratinolyzed peptide, conchiolinolyzed peptide, silk proteinolyzed peptide, soy bean protainolyzed peptide, wheat protainolyzed peptide, caseinolyzed peptide and the like; amino acids such as arginine, serine, glycine, threonine, glutamic acid, cisteine, methionine, leucine, tryptophane and the like; animal and vegetable extract components such as placenta extract, elastin, collagen, aloe extract, hamamelis extract, luffa water, chamomile extract, glycyrrhiza extract, black root extract and the like.

Examples of the thickening agent include polymer compounds such as guar gum, queens seed gum, xathane gum, carageenan, alginic acid, sodium carxobymethylcellulose, carboxyvinylpolymer, polyvinylpyrrolidone, ampholytic methacrylate copolymer, cationized cellulose, polyacrylate copolymer, nitrocellulose and the like.

Examples of the antioxidant include BHT, BHA, propyl gallate, d-α-tocopherol, d-δ-tocopherol, d,1-α-tocopherol, d-α-tocopherol acetate, d,1-α-tocopherol acetate, and the like.

Examples of the preservative include phenols, benzoic acid and salts thereof, halogenated bisphenols, acid amides, quarternary ammonium salts and the like.

Examples of the bactericide include trichlorocarbanide, zinc pyrithione, benzlconium chloride, benzethonium chloride, chlorhexidine, halocarbane, hinokitiol, phenol, isopropylphenol, photosensitive agents and the like.

Examples of the chelating agent include edetate salts, sodium oxalate and the like.

Examples of the pH regulator include citric acid, succinic acid, hydrochloric acid, ethanolamine, diethanolamine, triethanolamine, ammonia water, sodium hydroxide, calcium chloride and the like.

Examples of the ultraviolet absorber include benzophenone derivatives, p-aminobenzoic acid derivatives, p-methoxycinnamic acid derivatives, silicyllic acid derivatives, urocanic acid, urocanate, 4-tert-butyl-4'-methoxydibenzoylmethane, 2-(2'-hydroxy-5'-methylphenyl) benzotriazole, methyl anthranylate, rutin and derivatives thereof and the like.

Examples of the opacifier include kojic acid, arbutin, ascorbic acid, ascorbic glucoside, glutathione, elagic acid, placenta extract, orizanol, lucinol and the like.

Examples of the solvents include lower alcohols such as ethanol, propanol and the like; acetone, ethylene glycol monomethyl ether, toluene and the like.

Examples of the keratin ablation and resolution agent include salicylic acid, sulfur, resorcin, selenium oxide, pyridoxine and the like.

Examples of antipruritic include diphenhydramine hydrochloride, chlorpheramine maleate, camphor and the like.

Examples of the antiphlogistic agent include glycyrrhizinic acid and derivatives thereof, guaiazulene, hydrocortisone acetate, predonisone and the like.

Examples of the antiperspirant agent include aluminum hydroxychloride, aluminum chloride, zinc oxide, zinc p-phenolsulfonate and the like.

Examples of the refrigerant include menthol, methyl salicylate and the like.

Examples of the reductant include thioglycolic acid, cysteine and the like.

Examples of the antihistamic agent include diphedlamine hydrochloride, chlorphelamine maleate, glycyrrhetinic acid derivatives and the like.

Examples of the astringent include citric acid, tartaricacid, lactic acid, aluminumpotassiumsulfate, tannic acid and the like.

Examples of the stimulant include cantharis tincture, Shoyo tincture, capsicum tincture, benzyl nicotinate and the like.

Examples of the hair growth agent include swertia herb extract, cepharantin, vitamin E and derivatives thereof, ã-orizanol, capsicum tincture, Shoyo tincture, cantharis tincture, benzyl nicotinate, allantoin, photosentive agent 301, photosensitive agent 401 and the like.

Examples of the polymer powder include starch, nylon powder, polyethylene powder, polymethyl methacrylate, polyethylene terephthalate, polymethyl methacrylate laminated powder and the like.

Examples of the α-hydroxy acids and derivatives thereof include lactic acid, glycolic acid, fruit acid, hydroxycapric acid, long chain α-hydroxyfatty acid, long chain α-hydroxyfatty acid cholesteryl ester and the like.

Examples of the vitamins and derivatives thereof include vitamins such as vitamin A, vitamins B, vitamin D, vitamin E, panthotenic acid, biotinic acid and the like; vitamin derivatives such as ascorbyl stearate, ascorbyl palmitate, ascorbyl dipalmitate, ascorbyl tetraisopalmitate, magnesium ascorbyl phosphate, sodium ascorbate, tocopherol nicotinate, tocopherol acetate, tocopherol linolate, tocopherol ferulate and the like.

Examples of the saccharides and derivatives thereof include saccharides and derivatives thereof such as cyclodextrin, β-glucan, chithine, chitosan, glucose, trehalose, pectin, arabinogalactan, gelatin, dextrin, dextran and the like.

Examples of the organic acids include abietic acid, tartaric acid and the like.

Examples of the enzymes include lysozyme chloride, keratinase, papain, pancreatin, protease and the like.

Examples of the nucleic acid include adenosine triphosphate disodium and the like.

Examples of the hormones include estradiol, estron, ethynylestradiol, cortisone, hydrocortisone, predonizone and the like.

Examples of the clay minerals include montmorillonite, sericite, kaolinite, kaoline and the like.

Examples of the aromatic include limonene, linalool, citral, â-ionone, benzylbenzoate, indol, eugenol, auranthiol, geraniol, liral, damaskon, benzyl acetate, jasmine lactone, galacsolid, essential oil and the like.

Examples of the coloring agent include inorganic pigments such as mica, talk, kaolin, calcium carbonate, red iron oxide, yellow iron oxide, black iron oxide, ultramarine, iron blue, carbon black, titanium dioxide, zinc oxide, mica titanium, scale foil, boron nitride, photochromic pigment, synthetic fluorine gold mica, fine particle complex powder and the like; natural pigments such as β-carotene, calsamine, rutin, cochineal, chlorophyll and the like; organic synthetic coloring agents such as dyes, lake, organic pigments and the like.

In addition, components used in known cosmetics, medical products, food and the like can be appropriately compounded within the range in which the effect of the present invention does not decrease.

The cosmetic of the present invention can be produced by a usual method. Examples of cosmetics include basic cosmetics, make up cosmetics, hair cosmetics, aromatic cosmetics, body cosmetics and the like.

Examples of the basic cosmetics include washing materials such as cleansing foam, cleansing gel, washing powder, cleansing cream, cleansing milk, cleansing lotion, cleansing oil, cleansing mask and the like; lotions such as softening lotion, astringent lotion, washing lotion, multi-layer lotion and the like; emulsions such as emollient lotion, moisture lotion, milky lotion, nourishing lotion, nourishing milk, skin moisture, moisture emulsion, massage lotion, cleansing lotion, protect emulsion, sun protect, UV care milk, sun screen, make up lotion, keratin smoother, elbow lotion, hair milk, hand lotion, body lotion and the like; creams such as emollient cream, nourishing cream, burnishing cream, moisture cream, night cream, massage cream, cleansing cream, make up cream, base cream, pre-make up cream, sun screen cream, san tanning cream, hair remover, hair cream, deodorant cream, shaving cream, keratin softening cream and the like; gels such as cleansing gel, moisture gel and the like: soaps such as cosmetic soap, transparent soap, medical soap, liquid soap, shaving soap, synthetic cosmetic soap and the like; packs and masks such as peel off pack, powder pack, washing pack, oil pack, cleansing mask and the like; essences such as humectant essence, opacifying essence, ultraviolet ray preventing essence and the like.

Examples of the make up cosmetics include white powder dustings, foundations: lipsticks such as lipstick, lip gloss, lip cream and the like, cheek paint, eye liner, mascara, eye shadow, eye brow liner, eye blow, nail enamel, enamel remover, nail treatment and the like.

Examples of the hair cosmetics include shampoos such as oil shampoo, cream shampoo, conditioning shampoo, dandruff shampoo, rinse-in shampoo and the like; rinse; hair grow agent; hair foam, hair moose, hair spray, hair mist, hair gel, water grease, set lotion, color lotion, hair liquid, pomade, tic, hair cream, hair blow, branch coat, hair oil, permanent wave agent, hair dying agent, hair bleach and the like.

Examples of the aromatic cosmetics include aromatic, perfume, perfume, eau de perfume, eau de toilette, eau de cologne, paste aromatic, aromatic powder, aromatic soap, body lotion, bath oil and the like.

Examples of the body cosmetics include body washing materials such as body shampoo and the like; deodorizing cosmetics such as deodorant lotion, deodorant powder, deodorant spray, deodorant stick and the like; decolorant, dehairing and hair removing; bath additive; insect repellers such as insect preventing spray and the like.

Regarding the agent type, emulsion cosmetics in the form of oil in water (O/W) type, water in oil (W/O) type, W/O/W type and O/W/O type, oily cosmetics, solid cosmetics, liquid cosmetics, kneaded cosmetics, stick cosmetics, volatile oily cosmetics, powder cosmetics, jelly cosmetics, gel cosmetics, paste cosmetics, emulsified polymer cosmetics, sheet cosmetics, mist cosmetics, spray cosmetics and the like can be used.

An external agent is directly applied to skin in the form of an ointment, patch, lotion, liniment, liquid application agent and the like. The compounding amount of a dimerdiol ester to the external agent of the present invention is not particularly restricted. Preferably, it is from 0.1 to 50% by weight, particularly preferably from 0.5 to 30 wt %. Additives usually used in ointment, patch, lotion, liniment, liquid application agent and the like may be used.

The dimerdiol ester of monocarboxylic acid having 4 to 34 carbon atoms comprised in the oil materials of the present invention is excellent in safety, stability, hydrolysis-resistance, and gloss. Further, it can provide cosmetics and external agents, comprising the dimerdiol carboxylate, excellent in safety, stability, hydrolysis-resistance, pigment dispersability, gloss and feeling of use.

The dimerdiol ester with a dicarboxylic acid comprised in the oil materials of the present invention is excellent in safety, stability, pigment dispersability, and gloss. Further, it can provide cosmetics and external agents, comprising the dimerdiol carboxylate, excellent in safety, stability, pigment dispersability, gloss and feeling of use.

EXAMPLES

The following examples illustrate the present invention in more detail. These examples do not limit the scope of the present invention. All percents are by weight unless otherwise stated.

Synthesis Example 1 Production of a Dimerdiol

Into a 500 mL reaction vessel equipped with a stirrer, a thermometer and a gas-introducing tube were charged 140 g of methyl oleate, 60 g of methyl linoleate and 15 g of activated clay. After the inner air was replaced with nitrogen, the temperature was raised to 240° C. and a dimerization reaction was conducted for 6 hours. Then, the activated clay was removed by filtration and unreacted methyl ester of fatty acids were removed by distillation to obtain 134 g of dimethyl ester of dimer acids. Into a 500 mL auto clave was charged 125 g of the dimethyl ester of dimer acids thus obtained, and, thereto, 3 g of copper-chromium catalyst was added. Then, after the inner air was replaced with hydrogen, a hydrogenation was conducted at a pressure of 250 atmosphere, at 250° C. until no more hydrogen absorption was observed. For removing ether compounds and ester compounds, that is impurities, the hydrogenated product was subjected to a molecular distillation to obtain 97 g of a dimerdiol as the fraction of distillate at 237-252° C./0.1 torr. Acid value and hydroxyl value of the dimerdiol thus obtained were 0.2 and 196.0, respectively.

Example 1

Production of a Hydrogenated Rosin Dimerdiol Ester

Into a 1000 mL reaction vessel equipped with a stirrer, a thermometer and a gas-introducing tube were charged 158 g (0.46 mol) of hydrogenated rosin (KP-610, manufactured by Arakawa Chemical Industries, Ltd.) and 134 g (0.23 mol) of the dimerdiol obtained in Synthesis example 1. After the inner air was replaced with nitrogen, the temperature was raised to 240° C. and the reaction was conducted for 20 hours under a reduced pressure. After cooling, 160 g of heptane was added thereto and unreacted hydrogenated rosin was removed with an aqueous sodium hydroxide solution. The resulting mixture was washed with water, and heptane, the solvent in the mixture, was distilled off to obtain 227 g of aimed hydrogenated rosin dimerdiol ester. The obtained hydrogenated rosin dimerdiol ester is a viscous liquid at a normal temperature, and its acid value and hydroxyl value were 0.7 and 7.0, respectively.

Example 2

Production of a Hydrogenated Rosin Dimerdiol Ester

According to the same manner as in Example 1 except that 100 ppm of vitamin E (E-mix-D, manufactured by Eisai Co. Ltd.) based on the hydrogenated rosin dimerdiol ester was added after the washing with water, a tocopherol mixture added hydrogenated rosin dimerdiol ester was obtained. Analytical values thereof were the same as those in Example 1.

Example 3

Production of a Erucic Acid Dimerdiol Ester

Into a 1000 mL reaction vessel equipped with a stirrer, a thermometer and a gas-introducing tube were charged 160 g (0.46 mol) of erucic acid, 128 g (0.22 mol) of the dimerdiol obtained in Synthesis example 1, 1.2 g of para-toluene sulfonic acid and 200 g of heptane, and a dehydration was conducted at 110° C. for 7 hours under a nitrogen flow. After cooling, unreacted erucic acid was removed with an aqueous sodium hydroxide solution. The resulting mixture was washed with water, and heptane, the solvent in the mixture, was distilled off to obtain 191 g of aimed erucic acid dimerdiol ester. The obtained erucic acid dimerdiol ester is in a liquid state at a normal temperature, and its acid value, hydroxyl value and saponification value were 0.2, 2.1 and 92.8, respectively.

Example 4

Production of a Erucic Acid Dimerdiol Ester

According to the same manner as in Example 3 except that 100 ppm of d,l-α-tocopherol (manufactured by AJINOMOTO Co. Inc.) based on the erucic acid dimerdiol ester was added after the washing with water, a tocopherol mixture added hydrogenated rosin dimerdiol ester was obtained. Analytical values thereof were the same as those in Example 3.

Example 5

Production of a Mono-Isostearic Acid Dimerdiol Ester

Into a 1000 mL reaction vessel equipped with a stirrer, a thermometer and a gas-introducing tube were charged 94 g (0.33 mol) of isostearic acid, 180 g (0.33 mol) of dimerdiol (PESPOL HP-1000, manufactured by TOAGOSEI Co. Ltd.), 1.2 g of para-toluene sulfonic acid and 150 g of heptane, and a dehydration was conducted at 110° C. for 6 hours under a nitrogen flow. After cooling, unreacted isostearic acid was removed with an aqueous sodium hydroxide solution. The resulting mixture was washed with water, and heptane, the solvent in the mixture, was distilled off to obtain 221 g of aimed mono-isostearic acid dimerdiol ester. The obtained mono-isostearic acid dimerdiol ester is in a liquid state at a normal temperature, and its acid value, hydroxyl value and saponification value were 0.2, 62.1 and 66.5, respectively.

Example 6

Production of a Mono-Isostearic Acid Dimerdiol Ester

According to the same manner as in Example 5 except that 200 ppm of vitamin E (E-mix-D, manufactured by Eisai Co. Ltd.) based on the mono-isostearic acid dimerdiol ester was added after the washing with water, a tocopherol mixture added mono-isostearic acid dimerdiol ester was obtained. Analytical values thereof were the same as those in Example 5.

Example 7

Production of a Long Chain Branched Fatty Acid Dimerdiol Ester

Into a 1000 mL reaction vessel equipped with a stirrer, a thermometer and a gas-introducing tube were charged 175 g (0.55 mol) of long chain (Carbon number 10-31) branched fatty acid (FA-NH, manufactured by Nippon Fine Chemical Co. Ltd.), 159 g (0.28 mol) of dimerdiol (PESPOL HP-1000, manufactured by TOAGOSEI Co. Ltd.), 1.2 g of para-toluene sulfonic acid and 150 g of heptane, and a dehydration was conducted at 110° C. for 7 hours under a nitrogen flow. After cooling, unreacted long chain branched fatty acid was removed with an aqueous sodium hydroxide solution. The resulting mixture was washed with water, and heptane, the solvent in the mixture, was distilled off to obtain 261 g of aimed long chain branched fatty acid dimerdiol ester. The obtained long chain branched fatty acid dimerdiol ester is in a paste state at a normal temperature, and its acid value, hydroxyl value and saponification value were 0.7, 11.6 and 105.1, respectively.

Example 8

Production of a Long Chain Branched Fatty Fatty Acid Dimerdiol Ester

According to the same manner as in Example 7 except that 300 ppm of vitamin E (E-mix-D, manufactured by Eisai Co. Ltd.) based on the long chain branched fatty acid dimerdiol ester was added after the washing with water, a tocopherol mixture added long chain branched fatty acid dimerdiol ester was obtained. Analytical values thereof were the same as those in Example 7.

Example 9

Production of a Hydrogenated Rosin/Erucic Acid Dimerdiol Ester

Into a 1000 mL reaction vessel equipped with a stirrer, a thermometer and a gas-introducing tube were charged 47 g (0.14 mol) of hydrogenated rosin (KP-610, manufactured by Arakawa Chemical Industries, Ltd.), 48 g (0.14 mol) of erucic acid, 160 g (0.28 mol) of dimerdiol (PESPOL HP-1000, manufactured by TOAGOSEI Co. Ltd.). After inner air was replaced with nitrogen, a dehydration was conducted at 240° C. for 15 hours under a nitrogen flow. After cooling, unreacted acids were removed with an aqueous sodium hydroxide solution. The resulting mixture was washed with water, and heptane, the solvent in the mixture, was distilled off to obtain 225 g of aimed hydrogenated rosin/erucic acid dimerdiol ester. The obtained hydrogenated rosin/erucic acid dimerdiol ester is in a liquid state at a normal temperature, and its acid value and hydroxyl value were 0.1 and 7.6, respectively.

Example 10

Production of a Hydrogenated Rosin/Erucic Acid Dimerdiol Ester

According to the same manner as in Example 9 except that 300 ppm of vitamin E (E-mix-D, manufactured by Eisai Co. Ltd.) based on the hydrogenated rosin/erucic acid dimerdiol ester was added after the washing with water, a tocopherol mixture added hydrogenated rosin/erucic acid dimerdiol ester was obtained. Analytical values thereof were the same as those in Example 9.

Example 11

Production of a Isostearic Acid Dimerdiol Ester

Into a 2000 mL reaction vessel equipped with a stirrer, a thermometer and a gas-introducing tube were charged 311 g (1.04 mol) of isostearic acid, 287 g (0.52 mol) of dimerdiol (PESPOL HP-1000, manufactured by TOAGOSEI Co. Ltd.), 1.9 g of para-toluene sulfonic acid and 240 g of heptane, and a dehydration was conducted at 110° C. for 8 hours under a nitrogen flow. After cooling, unreacted isostearic acid was removed with an aqueous sodium hydroxide solution. The resulting mixture was washed with water, and heptane, the solvent in the mixture, was distilled off to obtain 523 g of aimed isostearic acid dimerdiol ester. The obtained isostearic acid dimerdiol ester is in a liquid state at a normal temperature, and its acid value, hydroxyl value and saponification value were 0.1, 7.1 and 105.5, respectively.

Example 12

Production of a Isostearic Acid Dimerdiol Ester

According to the same manner as in Example 11 except that 500 ppm of vitamin E (E-mix-D, manufactured by Eisai Co. Ltd.) based on the isostearic acid dimerdiol ester was added after the washing with water, a tocopherol mixture added isostearic acid dimerdiol ester was obtained. Analytical values thereof were the same as those in Example 11.

Reference Example 1

Oxidation stability of the dimerdiol esters obtained in Examples 1-12 were measured. Each of the measurement was conducted at 120° C., using 3 g of sample, at an air flow rate of 20 L/Hr with a Rancimat 676 type automatic oils and fats stability test apparatus (manufactured by Shibata/Metrohm Ltd.). Index of the oxidation stability was expressed by the time until conductance of the trapped water started rising. The results are shown in the following table.

TABLE

| Example No. | Dimerdiol ester | Index of oxidation stability |
|---|---|---|
| 1 | hydrogenated rosin dimerdiol ester | 6 hrs. |
| 2 | tocopherol mixture added hydrogenated rosin dimerdiol ester | 20 hrs. |
| 3 | erucic acid dimerdiol ester | 3 hrs. |
| 4 | tocopherol mixture added erucic acid dimerdiol ester | 27 hrs. |
| 5 | mono-isostearic acid dimerdiol ester | 8 hrs. |
| 6 | tocopherol mixture added mono-isostearic acid dimerdiol ester | 48 hrs. |
| 7 | long chain branched fatty acid dimerdiol ester | 4 hrs. |
| 8 | tocopherol mixture added long chain branched fatty acid dimerdiol ester | 30 hrs. |
| 9 | hydrogenated rosin/erucic acid dimerdiol ester | 4 hrs. |
| 10 | tocopherol mixture added hydrogenated rosin/erucic acid dimerdiol ester | 26 hrs. |
| 11 | isostearic acid dimerdiol ester | 8 hrs. |
| 12 | tocopherol mixture added isostearic acid dimerdiol ester | 48 hrs. or more |

The results indicate that any of the tested esters had sufficient oxidation stability to be used as a raw material for cosmetics, and addition of vitamin E further improves the oxidation stability.

Reference Example 2

Refractive index of the dimerdiol esters obtained in Examples 1, 3, 5, 7, 9 and 11 were measured. Each of the refractive index was measured at 30° C. using a refractometer Model 3 (Manufactured by ATAGO BUSSAN Ltd.). The results are shown in the following table.

TABLE

| Example No. | Dimerdiol ester | Refractive index |
|---|---|---|
| 1 | hydrogenated rosin dimerdiol ester | 1.5075 |
| 3 | erucic acid dimerdiol ester | 1.4719 |
| 5 | mono-isostearic acid dimerdiol ester | 1.4659 |
| 7 | long chain branched fatty acid dimerdiol ester | 1.4684 |
| 9 | hydrogenated rosin/erucic acid dimerdiol ester | 1.4892 |
| 11 | isostearic acid dimerdiol ester | 1.4709 |
|  | PESPOL HP-1000(manufactured by TOAGOSEI Co. Ltd.) | 1.4778 |
|  | liquid lanolin SS(manufactured by Nippon Fine Chemical Co. Ltd.) | 1.4878 |

The results indicate that any of the tested esters had refractive index similar to or higher than the refractive index of liquid lanolin SS, which is known as an oil material imparting good gloss. Hence, they have good gloss. It can be considered that this characteristic is caused by high refractive index of dimerdiol, the raw material.

Reference Example 3

Alkali hydrolysis resistance of the dimerdiol esters obtained in Examples 1, 3, 5, 7, 9 and 11 were measured. The alkali hydrolysis resistance was expressed by the decomposition ratio of 0.8 g of sample which was heated at 80° C. for 3 hours in 25 mL of 0.05 N of KOH-ethanol solution.

The results are shown in the following table.

TABLE

| Example No. | Dimerdiol ester | Decomposition ratio |
|---|---|---|
| 1 | hydrogenated rosin dimerdiol ester | 3% |
| 3 | erucic acid dimerdiol ester | 79% |
| 5 | mono-isostearic acid dimerdiol ester | 71% |
| 7 | long chain branched fatty acid dimerdiol ester | 73% |
| 9 | hydrogenated rosin/erucic acid dimerdiol ester | 33% |
| 11 | isostearic acid dimerdiol ester | 70% |
|  | glyceryl isooctanoate (manufactured by Nippon Fine Chemical Co. Ltd.) | 8% |

The results indicate that hydrogenated rosin dimerdiol ester exhibited a low decomposition ratio as same as that of glyceryl isooctanoate, which is known as an ester having good alkali hydrolysis resistance. Hence, it has good alkali hydrolysis resistance.

Example 13

According to the composition shown in the following Table and according to the following manner, an ointment was prepared.

Liquid paraffin, hydrogenated rosin/erucic acid dimerdiol ester obtained in Example 10, dimethyl siloxane and cetostearyl alcohol were heated up to 70° C. and mixed until a uniform mixture was obtained (oil phase).

Cetrimide and chlorocresol were dissolved in purified water at 70° C. To the aqueous solution thus obtained, the oil phase obtained above was added with stirring to make a uniform mixture, which was then cooled to room temperature to obtain an ointment.

TABLE

| Ingredient | Composition % by weight |
| --- | --- |
| liquid paraffin | 30.0 |
| hydrogenated rosin/erucic acid dimerdiol ester | 10.0 |
| dimethyl siloxane | 10.0 |
| cetostearyl alcohol | 5.0 |
| cetrimide | 0.5 |
| chlorocresol | 0.1 |
| purified water | balance |

Comparative Example 1

According to the same manner as in Example 13 except that hydrogenated rosin/erucic acid dimerdiol ester was replaced with glyceride tristearate, an ointment was prepared.

Example 14

According to the composition shown in the following Table and according to the following manner, an emollient cream was prepared.

Dipropylene glycol, glycerin and triethanolamine were dissolved in purified water, and heated up to 70° C. (water phase). Other ingredients were mixed at 70° C. (oil phase). To the water phase, the oil phase was added slowly with stirring. After stirring further, the obtained mixture was emulsified with an emulsifier and cooled to room temperature to obtain an emollient cream.

TABLE

| Ingredient | Composition % by weight |
| --- | --- |
| long chain branched fatty acid dimerdiol ester obtained in Example 8 | 7.0 |
| stearic acid | 3.0 |
| vaseline | 6.0 |
| cetyl alcohol | 5.0 |
| POE(20)-cetyl alcohol ether | 2.0 |
| propylene glycol monostearate | 3.0 |
| dipropylene glycol | 3.0 |
| glycerine | 3.0 |
| triethanolamine | 1.0 |
| antiseptic, antioxidant | q.s. |
| purified water | balance |

Comparative Example 2

According to the same manner as in Example 14 except that long chain branched fatty acid dimerdiol ester obtained in Example 8 was replaced with glyceryl tri-2-ethylhexanate, an emollient cream was prepared.

Example 15

According to the composition shown in the following Table and according to the following manner, a milky lotion was prepared.

Polyethylene glycol 1500, 1,3-butyleneglycol and triethanolamine were added to purified water, and dissolved by heating up to 70° C. (water phase). Other ingredients were mixed at 70° C. (oil phase). To the water phase, the oil phase was added slowly with stirring for pre-emulsification. The resulting mixture was further emulsified uniformly with an emulsifier and cooled to room temperature to obtain a milky lotion.

TABLE

| Ingredient | Composition % by weight |
| --- | --- |
| mono-isostearic acid dimerdiol ester obtained in Example 5 | 3.0 |
| stearic acid | 2.0 |
| vaseline | 3.0 |
| cetyl alcohol | 1.0 |
| sorbitan monooleate | 2.0 |
| polyethylene glycol 1500 | 3.0 |
| 1,3-butylene glycol | 5.0 |
| triethanolamine | 1.0 |
| perfume, preservative | q.s. |
| purified water | balance |

Comparative Example 3

According to the same manner as in Example 15 except that mono-isostearic acid dimerdiol ester obtained in Example 5 was replaced with glyceryl tri-2-ethylhexanate, a milky lotion was prepared.

Example 16

According to the composition shown in the following Table and according to the following manner, a liquid cream shampoo was prepared.

After purified water was heated up to 70° C., other ingredients were added thereto and dissolved uniformly. Then, the resulting mixture was cooled to obtain a liquid cream shampoo.

TABLE

| Ingredient | Composition % by weight |
| --- | --- |
| long chain branched fatty acid dimerdiol ester obtained in Example 8 | 2.0 |
| sodium polyoxyethylene(3) lauryl sulfate(30%) | 30.0 |
| sodium lauryl sulfate(30%) | 15.0 |
| lauric diethanolamide | 3.0 |
| polyethyleneglycol distearate | 2.0 |
| perfume, preservative | q.s. |
| sequestering agent, pH adjusting agent | q.s. |
| purified water | balance |

Comparative Example 4

According to the same manner as in Example 16 except that long chain branched fatty acid dimerdiol ester obtained in Example 8 was replaced with cetyl 2-ethylhexanate, a liquid cream shampoo was prepared.

Example 17

According to the composition shown in the following Table and according to the following manner, a hair conditioner was prepared.

Stearyl trimethylammonium chloride and presevative were dissolved in purified water by heating up to 70° C. to obtain an aqueous solution.

Erucic acid dimerdiol ester obtained in Example 4, glyceryl monostearate, cetyl alcohol, glycerin and perfume were mixed at 70° C. with stirring. The mixture was added to the aqueous solution obtained above, and mixed thoroughly with stirring, followed by cooling to prepare a hair conditioner.

TABLE

| Ingredient | Composition % by weight |
|---|---|
| erucic acid dimerdiol ester obtained in Example 4 | 2.0 |
| stearyl trimethylammonium chloride | 3.0 |
| glyceryl monostearate | 0.5 |
| cetyl alcohol | 3.0 |
| glycerin | 3.0 |
| perfume, preservative | q.s. |
| purified water | balance |

Comparative Example 5

According to the same manner as in Example 17 except that Erucic acid dimerdiol ester obtained in Example 4 was replaced with beef tallow fatty acid glyceride, a hair conditioner was prepared.

Example 18

According to the composition shown in the following Table and according to the following manner, a lipstick was prepared.

Titanium dioxide, Red No. 201 and Red No. 202 were added to a portion of mono-isostearic acid dimerdiol ester obtained in Example 5. The mixture was kneaded with a roller and mixed uniformly (pigment portion).

Red No. 223 was dissolved in the remaining mono-isostearic acid dimerdiol ester obtained in Example 5 (dye portion). Other ingredients were mixed and fused by heating, and, thereto the pigment portion and dye portion were added and dispersed uniformly by a homomixer. Then, the dispersion was put in a mold and cooled rapidly to make a stick.

TABLE

| Ingredient | Composition % by weight |
|---|---|
| hydrogenated rosin dimerdiol ester obtained in Example 1 | 13.0 |
| trimethylol propane triisostearate | 16.0 |
| mono-isostearic acid dimerdiol ester obtained in Example 5 | 31.0 |
| beeswax | 9.0 |
| lanolin | 6.0 |
| carnauba wax | 7.0 |
| ceresine | 6.0 |
| hard lanolin fatty acid cholesteryl ester | 5.0 |
| titanium dioxide | 5.0 |
| Red No.201 | 0.6 |
| Red No.202 | 1.2 |
| Red No.223 | 0.2 |
| perfume, preservative | q.s. |

Comparative Example 6

According to the same manner as in Example 18 except that hydrogenated rosin dimerdiol ester obtained in Example 1 was replaced with di-isostearyl malic acid, and mono-isostearic acid dimerdiol ester obtained in Example 5 was replaced with a caster oil, a lipstick was prepared.

Reference Example 4

Stability at 40° C. of the ointments prepared in Example 13 and Comparative example 1, the emollient creams prepared in Example 14 and Comparative example 2, the milky lotions prepared in Example 15 and Comparative example 3, the shampoos prepared in Example 16 and Comparative example 4 and the hair conditioners prepared in Example 17 and Comparative example 5 were evaluated. The results according to the following criteria are shown in the following Table.

TABLE

| Tested Sample | stability |
|---|---|
| ointments in Example 13 | ○ |
| emollient creams in Example 14 | ○ |
| milky lotions in Example 15 | ○ |
| shampoos in Example 16 | ○ |
| hair conditioner in Example 17 | ○ |
| ointments in Comparative example 1 | Δ |
| emollient creams in Comparative example 2 | ○ |
| milky lotions in Comparative example 3 | Δ |
| shampoos in Comparative example 4 | Δ |
| hair conditioner in Comparative example 5 | ○ |

"○": Stable even after 30 days from preparation.
"Δ": Phase separation or deposition was observed on 10-29 days after preparation.
"X": Phase separation or deposition was observed within 10 days after preparation.

The results show that stability of the ointments, milky lotions and shampoos prepared in Examples 13-17 are better than those prepared in Comparative examples 1-5.

Reference Example 5

Female panelists were requested to use-test the ointments prepared in Example 13 and Comparative example 1, the emollient creams prepared in Example 14 and Comparative example 2 and the milky lotions prepared in Example 15 and Comparative example 3. The results according to the following criteria are shown in the following table.

TABLE

| | Examples | | | Comparative examples | | |
|---|---|---|---|---|---|---|
| | 13 | 14 | 15 | 1 | 2 | 3 |
| [Feeling of use] | | | | | | |
| Non-sticky feel | ◎ | ◎ | ○ | ○ | ○ | ○ |
| Dry feeling | ○ | ◎ | ◎ | ○ | ○ | ○ |
| Smooth feel | ◎ | ◎ | ◎ | ○ | Δ | ○ |
| [Durability] | | | | | | |
| Non-sticky feel | ◎ | ◎ | ○ | ○ | ○ | ○ |
| Dry feeling | ○ | ◎ | ◎ | ○ | ○ | ○ |
| Smooth feel | ◎ | ◎ | ◎ | ○ | Δ | ○ |

[Feeling of use]
"◎": excellent
"○": good
"Δ": insufficient
"X": bad
[Durability]: Feeling of use after used for 5 hours
"◎": excellent
"○": good
"Δ": insufficient
"X": bad The results show that Feeling of use and Durability of the ointments, emollient creams and milky lotions of the present invention are excellent.

Reference Example 6

Female panelists were requested to use-test the shampoos prepared in Example 16 and Comparative example 4 and the hair conditioners prepared in Example 17 and Comparative example 5. Sensory evaluations were conducted about moist feel, softness, gloss and manageability of hair. The results according to the following criteria are shown in the following table.

TABLE

|  | Moist feel | Softness | gloss | manageability |
|---|---|---|---|---|
| shampoo of Example 16 | ◎ | ◎ | ◎ | ○ |
| hair conditioner of Example 17 | ◎ | ◎ | ◎ | ○ |
| shampoo of Comparative example 4 | Δ | ○ | Δ | Δ |
| hair conditioner of Comparative example 5 | Δ | ○ | Δ | ○ |

[Moist feel]
"◎": excellent
"○": good
"Δ": fair
"X": not moist
[Softness]
"◎": very soft
"○": soft
"Δ": middle of soft and hard
"X": hard
[gloss]
"◎": very gloss
"○": glossy
"Δ": little glossy
"X": not glossy
[manageability]
"◎": excellent
"○": good
"Δ": fair
"X": bad The results show that Feeling of use of the Shampoo and hair conditioner of the present invention are excellent.

Reference Example 7

Female panelists were requested to use-test the lipsticks prepared in Example 18 and Comparative example 6. Sensory evaluations were conducted about moist feel, adhesiveness, Spreadability, gloss, oxidation stability and perspiration. The results according to the following criteria are shown in the following table.

TABLE

| [Feeling of use] | Lip stick of Example 18 | Lip stick of Comparative example 6 |
|---|---|---|
| moist feel | ◎ | Δ |
| adhesiveness | ◎ | Δ |
| spreadability | ○ | ○ |
| gloss | ◎ | Δ |
| Oxidation stability | ◎ | ○ |
| Perspiration | ○ | Δ |

[Moist feel]
"◎": excellent
"○": good
"Δ": fair

TABLE-continued

| [Feeling of use] | Lip stick of Example 18 | Lip stick of Comparative example 6 |
|---|---|---|

"X": not moist
[Adhesiveness]
"◎": excellent
"○": good
"Δ": in-between good and bad
"X": bad
[Spreadability]
"◎": excellent
"○": good
"Δ": in-between good and bad
"X": bad
[gloss]
"◎": very glossy
"○": glossy
"Δ": little glossy
"X": not glossy
[oxidation stability]
Change of odor was evaluated after leaving in an oven at 40° C. for 3 months.
"○": No change was observed.
"X": A clear change was observed.
[perspiration]
"○": No perspiration was observed for 2 months or longer.
"Δ": No perspiration was observed for 2 weeks or longer.
"X": Perspiration was observed within 2 weeks.

The results show that the lipstick of the present invention are excellent in Feeling of use and perspires little.

Examples 19-27

Compounding dimerdiol esters of the present invention, foundations, sunscreen agents, mascara, eye shadows and lipsticks were produced. All products exhibited good stability and usability. The formulas and processes for the productions are shown below.

Example 19 Powdery Foundation

| No. | Ingredient | Composition % by weight |
|---|---|---|
| 1. | talc | 15.0 |
| 2. | mica | 30.0 |
| 3. | kaolin | 15.0 |
| 4. | titanium dioxide | 15.0 |
| 5. | titanated mica | 3.0 |
| 6. | zinc stearate | 1.0 |
| 7. | nylon powder | 5.0 |
| 8. | red iron oxide | 1.0 |
| 9. | yellow iron oxide | 3.0 |
| 10. | black iron oxide | 0.2 |
| 11. | squalane | 6.0 |
| 12. | hydrogenated rosin dimerdiol ester obtained in Example 2 | 1.0 |
| 13. | octyldodecyl myristate | 2.0 |
| 14. | neopentylglycol diisooctanoate | 2.0 |
| 15. | sorbitan monooleate | 0.5 |
| 16. | preservative | q.s. |
| 17. | antioxidant | q.s. |
| 18. | perfume | q.s. |

Above ingredients No. 1 and No. 8-10 were mixed with henshel type mixer. Then, ingredients 2-7 were added thereto and mixed thoroughly. The resulting mixture and a mixture which was prepared by mixing ingredients 12-18 with heating to 70° C. were mixed and crushed to obtain aimed powdery foundation.

Example 20 Milky Foundation

| No. | Ingredient | Composition % by weight |
|---|---|---|
| 1. | ion-exchanged water | 60.9 |
| 2. | dispersant | 0.1 |
| 3. | dipropylene glycol | 5.0 |
| 4. | preservative | q.s. |
| 5. | polyoxyethylene modified dimethylpolysiloxane | 4.0 |
| 6. | decamethylcyclopentasiloxane | 12.0 |
| 7. | isostearic acid dimerdiol ester obtained in Example 12 | 5.0 |
| 8. | zinc white | 10.0 |
| 9. | sericite | 0.36 |
| 10. | titanium dioxide | 8.32 |
| 11. | yellow iron oxide | 0.80 |
| 12. | red iron oxide | 0.36 |
| 13. | black iron oxide | 0.16 |
| 14. | perfume | q.s. |

Above ingredients No. 1-4 were mixed with heating, and, thereto, ingredients No. 9-13 were added and dispersed. Then, the resulting was heated to 70° C. and mixed with ingredients 5-7, followed by carrying out emulsification. Then, the emulsified mixture was cooled to room temperature and, thereto, ingredient 14 was added to obtain aimed milky foundation.

Example 21 Dual-Use Foundation

| No. | Ingredient | Composition % by weight |
|---|---|---|
| 1. | silicon treated talc | 19.0 |
| 2. | silicon treated mica | 40.0 |
| 3. | silicon treated titanium dioxide | 5.0 |
| 4. | zinc white | 15.0 |
| 5. | silicon treated red iron oxide | 1.0 |
| 6. | silicon treated yellow iron oxide | 3.0 |
| 7. | silicon treated black iron oxide | 0.2 |
| 8. | zinc stearate | 0.1 |
| 9. | nylon powder | 2.0 |
| 10. | monoisostearic acid dimerdiol ester obtained in Example 6 | 4.0 |
| 11. | solid paraffin | 0.5 |
| 12. | dimethyl polysiloxane | 4.0 |
| 13. | glyceryl triisooctaonate | 5.0 |
| 14. | octyl methoxycinnamate | 1.0 |
| 15. | preservative | q.s. |
| 16. | antioxidant | q.s. |
| 17. | perfume | q.s. |

Above ingredients No. 1-9 were mixed with henshel type mixer. Then, the resulting mixture and a mixture which was prepared by mixing ingredients 10-17 with heating to 70° C. were mixed and crushed to obtain aimed foundation.

Example 22 Oily Stick Foundation

| No. | Ingredient | Composition % by weight |
|---|---|---|
| 1. | talc | 15.0 |
| 2. | titanium oxide | 7.0 |
| 3. | kaolin | 20.0 |
| 4. | mica | 3.3 |
| 5. | red iron oxide | 1.0 |
| 6. | yellow iron oxide | 3.0 |
| 7. | black iron oxide | 0.2 |
| 8. | solid paraffin | 3.0 |
| 9. | micro crystaline wax | 7.0 |
| 10. | vaseline | 14.0 |
| 11. | phytosteryl/isostearyl dimerdilinoleate (PHY/IS-DA, manufactured by Nippon Fine Chemical Co. Ltd.) | 1.0 |
| 12. | dimethyl polysiloxane | 3.0 |
| 13. | monoisostearic acid dimerdiol ester obtained in Example 6 | 5.0 |
| 14. | isopropyl palmitate | 17.0 |
| 15. | antioxidant | q.s. |
| 16. | perfume | q.s. |

Above ingredients No. 8-15 were mixed at 85° C., and ingredients No. 1-7 were added thereto, mixed by a disper and dispersed with a colloid mill. Ingredient 16 was added to the resulting mixture, and, after being de-gassed, the mixture was poured to a vessel at 70° C. and cooled.

Example 23 Sunscreen Agent

| No. | Ingredient | Composition % by weight |
|---|---|---|
| 1. | ultra fine particle titanium oxide | 5.0 |
| 2. | ion-exchanged water | 54.95 |
| 3. | 1,3-butylene glycol | 7.0 |
| 4. | EDTA-2Na | 0.05 |
| 5. | triethanolamine | 1.0 |
| 6. | oxybenzone | 2.0 |
| 7. | octyl paramethoxycinnamate | 5.0 |
| 8. | squalane | 9.0 |
| 9. | long chain branched fatty acid dimerdiol ester obtained in Example 8 | 5.0 |
| 10. | phytosteryl/isostearyl dimerdilinoleate (PHY/IS-DA, manufactured by Nippon Fine Chemical Co. Ltd.) | 1.0 |
| 11. | stearyl alcohol | 3.0 |
| 12. | stearic acid | 3.0 |
| 13. | glyceryl monostearate | 3.0 |
| 14. | polyethylacrylate | 1.0 |
| 15. | preservative | q.s. |
| 16. | antioxidant | q.s. |
| 17. | perfume | q.s. |

Above ingredients No. 2-5 were mixed at 70° C., and ingredients No. 1 was added thereto and dispersed thoroughly. Then, the resulting mixture and a mixture which was prepared by mixing ingredients 6-17 with heating were mixed and emulsified with a homogenizer. Thereafter, the resulting was cooled with stirring to obtain aimed sunscreen agent.

Example 24 Mascara

| No. | Ingredient | Composition % by weight |
|---|---|---|
| 1. | black iron oxide | 10.0 |
| 2. | hydrogenated rosin dimerdiol ester obtained in Example 2 | 20.0 |
| 3. | polyacrylic acid ester emulsion | 20.0 |
| 4. | solid paraffin | 8.0 |
| 5. | lanolin wax | 8.0 |
| 6. | light isoparaffin | 17.0 |
| 7. | sorbitan sesquioleate | 3.0 |

| No. | Ingredient | Composition % by weight |
|---|---|---|
| 8. | purified water | 10.0 |
| 9. | 2-ethylhexyl-p-cinnamate | 3.0 |
| 10. | preservative | q.s. |
| 11. | perfume | q.s. |

Oily ingredients No. 2-7, 9, 10 and 11 were mixed with heating. (oil part) To the oil part, ingredient 1 was added and dispersion treatment was conducted. Then, heated ingredient 8 was added to the oil part, and further dispersion treatment, then cooling, were conducted to obtain aimed mascara.

Example 25 Milky Eye Shadow

| No. | Ingredient | Composition % by weight |
|---|---|---|
| 1. | talc | 10.0 |
| 2. | kaolin | 4.0 |
| 3. | pigment | 5.0 |
| 4. | hydrogenated rosin dimerdiol ester obtained in Example 2 | 17.0 |
| 5. | phytosteryl/isostearyl dimerdilinoleate (PHY/IS-DA, manufactured by Nippon Fine Chemical Co. Ltd.) | 3.0 |
| 6. | stearic acid | 7.0 |
| 7. | isopropyl myristate | 1.0 |
| 8. | liquid paraffin | 4.0 |
| 9. | propylene glycol monolaurate | 1.5 |
| 10. | antioxidant | q.s. |
| 11. | perfume | q.s. |
| 12. | purified water | 45.0 |
| 13. | butylene glycol | 5.0 |
| 14. | light isoparaffin | 1.0 |
| 15. | 2-ethylhexyl-p-cinnamate | 5.0 |
| 16. | preservative | q.s. |
| 17. | triethanol amine | 1.0 |
| 18. | sequestering agent | q.s. |

Above ingredients No. 4-9 and 16 were mixed with heating to 70° C., and ingredients No. 14 and 15 were added thereto. (oil part) Ingredients 13, 17 and 18 were dissolved in ingredient 12, and ingredients 1, 2 and 3 were added thereto, thoroughly dispersed and heated to 70-80° C. (water part)

Then, the water part was added to the oil part and emulsified. Using an emulsifier, emulsified particles were adjusted, and cooling and de-gassing were conducted to obtain aimed milky eye shadow.

Example 26

Lipstick

| Ingredient | Composition % by weight |
|---|---|
| 1. ceresine | 5.0 |
| 2. paraffin wax | 10.0 |
| 3. candelira wax | 3.0 |
| 4. carnauba wax | 2.0 |
| 5. lanolin fatty acid cholesteryl ester (YOFCO CLE-S, manufactured by Nippon Fine Chemical Co. Ltd.) | 5.0 |
| 6. phytosteryl/isostearyl dimerdilinoleate (PHY/IS-DA, manufactured by Nippon Fine Chemical Co. Ltd.) | 1.0 |
| 7. isostearic acid dimerdiol ester obtained in Example 11 | 15.0 |

| Ingredient | Composition % by weight |
|---|---|
| 8. mono-isostearic acid dimerdiol ester obtained in Example 5 | 28.8 |
| 9. polyether modified silicone | 10.0 |
| 10. perfluoro polyether (FOMBLIN HC-04) | 5.0 |
| 11. red No. 201 | 1.0 |
| 12. red No. 202 | 2.0 |
| 13. yellow No. 4 A1 lake | 1.0 |
| 14. titanium oxide | 1.0 |
| 15. lecithin | 0.5 |
| 16. vitamin A | 0.5 |
| 17. antioxidant | 0.1 |
| 18. perfume | 0.1 |

Ingredients 11-14 were added to a portion of ingredient 7 and kneaded with a roller to make the mixture uniform. After adding other ingredients thereto, mixing by heating, the mixture was poured to a mold and cooled rapidly to obtain aimed lipstick.

Example 27

Lipgloss

| Ingredient | Composition % by weight |
|---|---|
| 1. dextrin palmitate | 10.0 |
| 2. hydrogenated rosin dimerdiol ester obtained in Example 1 | 30.0 |
| 3. macadamia nut oil fatty acid cholesteryl ester (YOFCO MAC, manufactured by Nippon Fine Chemical C. Ltd.) | 10.0 |
| 4. phytosteryl/isostearyl dimerdilinoleate (PHY/IS-DA, manufactured by Nippon Fine Chemical Co. Ltd.) | 10.0 |
| 5. methyl phenyl polysiloxane | 30.0 |
| 6. glyceryl tri-2-ethylhexanoate | 5.0 |
| 7. liquid paraffin | 5.0 |

Whole ingredients were heated, fused and mixed. Then, the mixture was poured in a vessel, then, cooled and solidified to obtain aimed lipgloss.

Example 28

Production of an Ester of Dimerdiol and Dimer Acid

Into a 500 mL reaction vessel equipped with a stirrer, a thermometer and a gas-introducing tube were charged 75 g (0.1364 mol) of dimerdiol (PESPOL HP-1000, manufactured by TOAGOSEI Co. Ltd.) and 39.1 g (0.0682 mol) of dimer acid (Empol 1061, manufactured by Henkel Co. Ltd.). After inner air was replaced with nitrogen, the temperature was raised to 220° C. and an esterification was conducted at 220-230° C. for 6 hours under a nitrogen flow and reduced pressure (133-220 hPa). 107.7 g of aimed dimerdiol/dimer acid ester was obtained. Hereinafter, this ester is referred to as "DD-DA/1:0.5". The ester properties of DD-DA/1:0.5 are as follows.

acid value: 1.44,
hydroxyl value: 70.8,
saponification value: 72.5
$M_n$*: 2,600, $M_w$*: 5,200

Hereinafter, Mn and Mw indicate number average molecular weight and weight average molecular weight measured by Gel permeation chromatography (GPC).

Example 29

Production of an Ester of Dimerdiol and Dimer Acid

Into a 500 mL reaction vessel equipped with a stirrer, a thermometer and a gas-introducing tube were charged 60.0 g (0.109 mol) of dimerdiol (PESPOL HP-1000, manufactured by TOAGOSEI Co. Ltd.) and 43.8 g (0.0764 mol) of dimer acid (Empol 1061, manufactured by Henkel Co. Ltd.). After inner air was replaced with nitrogen, the temperature was raised to 220° C. and an esterification was conducted at 220-230° C. for 6 hours under a nitrogen flow and reduced pressure (133-220 hPa). To the resulting product, 300 ppm of vitamin E (E-mix-D, manufactured by Eisai Co. Ltd. All vitamin E used in the Examples and Comparative examples below are the same as that used in this Example.) was added to obtain 95.7 g of aimed dimerdiol/dimer acid ester. Hereinafter, this ester is referred to as "DD-DA/1:0.7". The ester properties of DD-DA/1:0.7 are as follows.
acid value: 1.62,
hydroxyl value: 39.3,
saponification value: 86.4
Mn: 3,400, Mw: 9,500

Example 30

Production of an Ester of Dimerdiol and Hydrogenated Dimer Acid

Into a 1000 mL reaction vessel equipped with a stirrer, a thermometer and a gas-introducing tube were charged 250.0 g (0.455 mol) of dimerdiol (PESPOL HP-1000, manufactured by TOAGOSEI Co. Ltd.) and 130.8 g (0.227 mol) of dimer acid (Empol 1008, manufactured by Henkel Co. Ltd.). After inner air was replaced with nitrogen, the temperature was raised to 220° C. and an esterification was conducted at 220-230° C. for 6 hours under a nitrogen flow and reduced pressure (133-213 hPa). To the resulting product, 300 ppm of vitamin E was added to obtain 362.9 g of aimed dimerdiol/dimer acid ester. Hereinafter, this ester is referred to as "DD-HDA/1:0.5". The ester properties of DD-HDA/1:0.5 are as follows.
acid value: 1.09,
hydroxyl value: 65.5,
saponification value: 57.7
Mn: 2,500, Mw: 4,900

Example 31

Production of an Ester of Dimerdiol and Hydrogenated Dimer Acid

Into a 1000 mL reaction vessel equipped with a stirrer, a thermometer and a gas-introducing tube were charged 200.0 g (0.364 mol) of dimerdiol (PESPOL HP-1000, manufactured by TOAGOSEI Co. Ltd.) and 146.5 g (0.255 mol) of dimer acid (Empol 1008, manufactured by Henkel Co. Ltd.). After inner air was replaced with nitrogen, the temperature was raised to 220° C. and an esterification was conducted at 220-230° C. for 6 hours under a nitrogen flow and reduced pressure (133-213 hPa). To the resulting product, 300 ppm of vitamin E was added to obtain 327.2 g of aimed dimerdiol/ dimer acid ester. Hereinafter, this ester is referred to as "DD-HDA/1:0.7". The ester properties of DD-HDA/1:0.7 are as follows.
acid value: 1.37,
hydroxyl value: 33.9,
saponification value: 86.4
Mn: 3,800, Mw: 8,200

Example 32

Production of an Ester of Dimerdiol and Hydrogenated Dimer Acid

Into a 2000 mL reaction vessel equipped with a stirrer, a thermometer, a gas-introducing tube and a reflux condenser were charged 200.0 g (0.364 mol) of dimerdiol (PESPOL HP-1000, manufactured by TOAGOSEI Co. Ltd.), 146.5 g (0.255 mol) of dimer acid (Empol 1008, manufactured by Henkel Co. Ltd.), 350 ml of n-heptane and 3.5 g of para-toluene sulfonic acid, as a catalyst. The mixture was heated up to 110-115° C., and the reaction was conducted for 8 hours under nitrogen flow, while heating and refluxing the solvent and distilling out the produced water. Then, the resulting mixture was cooled to 70-80° C., and treated with alkali, the amount being more than that required for neutralizing the catalyst. After washing with water for deacidification, removing the solvent under reduced pressure, successively, 300 ppm of vitamin E was added thereto to obtain 330.3 g of aimed dimerdiol/dimer acid ester. Hereinafter, this ester is referred to as "DD-HDAS/1:0.7". The ester properties of DD-HDAS/1:0.7 are as follows.
acid value: 0.3,
hydroxyl value: 33.0,
saponification value: 85.2
Mn: 3,700, Mw: 8,000

Example 33

Production of an Ester of Dimerdiol and Sebacic Acid

Into a 1000 mL reaction vessel equipped with a stirrer, a thermometer and a gas-introducing tube were charged 280.0 g (0.509 mol) of dimerdiol (PESPOL HP-1000, manufactured by TOAGOSEI Co. Ltd.) and 51.6 g (0.255 mol) of sebacic acid (manufactured by KOKURA SYNTHETIC INDUSTRIES, Ltd.). After inner air was replaced with nitrogen, the temperature was raised to 220° C. and an esterification was conducted at 220-230° C. for 5 hours under a nitrogen flow and reduced pressure (133-213 hPa). To the resulting product, 300 ppm of vitamin E was added to obtain 308.1 g of aimed dimerdiol/sebacic acid ester. Hereinafter, this ester is referred to as "DD-SEBA/1:0.5". The ester properties of DD-SEBA/1:0.5 are as follows.
acid value: 1.34,
hydroxyl value: 92.7,
saponification value: 77.1
Mn: 1,600, Mw: 3,300

Example 34

Production of an Ester of Dimerdiol and Sebacic Acid

Into a 1000 mL reaction vessel equipped with a stirrer, a thermometer and a gas-introducing tube were charged 250.0 g (0.455 mol) of dimerdiol (PESPOL HP-1000, manufactured by TOAGOSEI Co. Ltd.) and 64.5 g (0.318 mol) of sebacic acid (manufactured by KOKURA SYNTHETIC INDUSTRIES, Ltd.). After inner air was replaced with nitrogen, the temperature was raised to 220° C. and an esterification was conducted at 220-230° C. for 5 hours under a nitrogen flow and reduced pressure (133-213 hPa). To the resulting product, 300 ppm of vitamin E was added to obtain 288.8 g of aimed dimerdiol/sebacic acid ester. Hereinafter, this ester is referred to as "DD-SEBA/1:0.7". The ester properties of DD-SEBA/1:0.7 are as follows.
- acid value: 1.48,
- hydroxyl value: 58.0,
- saponification value: 128.8
- Mn: 2,200, Mw: 5,500

Example 35

Production of an Ester of Dimerdiol and Hydrogenated Dimer Acid

Into a 2000 mL reaction vessel equipped with a stirrer, a thermometer, a gas-introducing tube and a reflux condenser were charged 200.0 g (0.364 mol) of dimerdiol (PESPOL HP-1000, manufactured by TOAGOSEI Co. Ltd.), 51.6 g (0.255 mol) of sebacic acid (manufactured by KOKURA SYNTHETIC INDUSTRIES, Ltd.), 350 ml of n-heptane and 3.5 g of para-toluene sulfonic acid, as a catalyst. The mixture was heated up to 110-115° C., and the reaction was conducted for 8 hours under nitrogen flow, while heating and refluxing the solvent and distilling out the produced water. Then, the resulting mixture was cooled to 70-80° C., and treated with alkali, the amount being more than that required for neutralizing the catalyst. After washing with water for deacidification, removing the solvent under reduced pressure, successively, 300 ppm of vitamin E was added thereto to obtain 220.0 g of aimed dimerdiol/sebacic acid ester. Hereinafter, this ester is referred to as "DD-SEBAS/1:0.7". The ester properties of DD-SEBAS/1:0.7 are as follows.
- acid value: 0.3,
- hydroxyl value: 60.3,
- saponification value: 125.0
- Mn: 2,100, Mw: 3,300

Reference Example 8

Oxidation stability of the esters obtained in Examples 28-35 were measured. Each of the measurement was conducted at 120° C., using 3 g of sample, at an air flow rate of 20 L/Hr with a Rancimat 676 type automatic oils and fats stability test apparatus (manufactured by Shibata/Metrohm Ltd.). Index of the oxidation stability was expressed by the time until conductance of the trapped water started rising. The results are shown in the following table.

TABLE

| Example No. | Ester | Index of oxidation stability |
|---|---|---|
| 28 | DD-DA/1:0.5 | 10 hrs. |
| 29 | DD-DA/1:0.7 | 15 hrs. |
| 30 | DD-HDA/1:0.5 | 14 hrs. |
| 31 | DD-HDA/1:0.7 | 20 hrs. |
| 32 | DD-HDAS/1:0.7 | 21 hrs. |
| 33 | DD-SEBA/1:0.5 | 15 hrs. |
| 34 | DD-SEBA/1:0.7 | 23 hrs. |
| 35 | DD-SEBAS/1:0.7 | 25 hrs. |

The results indicate that any of the tested esters of the present invention were stable more than 10 hours, and had sufficient oxidation stability.

Reference Example 9

Refractive index of the esters obtained in Examples 28-35 were measured. Each of the refractive index was measured at 20° C. using a refractometer Model 3 (Manufactured by ATAGO BUSSAN Ltd.). The results are shown in the following table.

TABLE

| Example No. | Ester | Refractive index |
|---|---|---|
| 28 | DD-DA/1:0.5 | 1.4867 |
| 29 | DD-DA/1:0.7 | 1.4876 |
| 30 | DD-HDA/1:0.5 | 1.4844 |
| 31 | DD-HDA/1:0.7 | 1.4848 |
| 32 | DD-HDAS/1:0.7 | 1.4846 |
| 33 | DD-SEBA/1:0.5 | 1.4830 |
| 34 | DD-SEBA/1:0.7 | 1.4833 |
| 35 | DD-SEBAS/1:0.7 | 1.4835 |
| liquid lanolin SS (manufactured by Nippon Fine Chemical Co. Ltd.) | | 1.4930 |
| di-iostearyl malate (manufactured by Nissin Oil Mills Ltd.) | | 1.4611 |

The results indicate that any of the tested esters of the present invention had refractive index similar to the refractive index of liquid lanolin SS, which is known as an oil imparting good gloss. Hence, they have good gloss.

Reference Example 10

Dispersability for pigment, titanium dioxide, red iron oxide and organic pigment Red No. 202, of the esters obtained in Examples 28-35, polybutene (PARLEAM 18, manufactured by NOF CORP.) and di-isostearyl malate (Cosmol 222, manufactured by Nissin Oil Mills Ltd.) were measured. Titanium dioxide, red iron oxide and organic pigment used in the measurement are PIGMOLITE CR-50, PIGMOLITE BENGARA No. 211 and Red 202, respectively, manufactured by DAITO KASEI KOGYO Co. Ltd. The dispersability is expressed by amount (g) of the tested sample per 100 g of the pigment at wet point (W.P) and flow point (F.P).

TABLE

| Ester | Titanium dioxide | | Red iron oxide | | Red 202 | |
|---|---|---|---|---|---|---|
| | W.P | F.P | W.P | F.P | W.P | F.P |
| DD-DA/1:0.5 | 45 | 97 | 69 | 224 | 120 | 165 |
| DD-DA/1:0.7 | 66 | 86 | 76 | 172 | 140 | 175 |
| DD-HDA/1:0.5 | 57 | 105 | 70 | 230 | 119 | 163 |
| DD-HDA/1:0.7 | 64 | 114 | 80 | 193 | 142 | 177 |
| DD-HDAS/1:0.7 | 66 | 117 | 75 | 200 | 138 | 170 |
| DD-SEBA/1:0.5 | 44 | 97 | 73 | 252 | 105 | 156 |
| DD-SEBA/1:0.7 | 66 | 95 | 75 | 229 | 117 | 149 |
| DD-SEBAS/1:0.7 | 63 | 98 | 78 | 210 | 148 | 150 |
| Ester obtained in Example 2 | 53 | 83 | 71 | 195 | 123 | 172 |
| Ester obtained in Example 6 | 29 | 82 | 61 | 168 | 95 | 188 |
| polybutene | 55 | 100 | 68 | 236 | 116 | 198 |
| di-iostearyl malate | 26 | 55 | 63 | 188 | 106 | 200 |

The results indicate that any of the tested esters of the present invention are superior in dispersability for titanium dioxide to polybutene, and superior in dispersability for red iron oxide to polybutene and di-iostearyl malate.

Reference Example 11

Esters obtained in Examples 28-35, liquid lanolin (YOFCO Liquid lanolin SS, manufactured by Nippon Fine Chemical Co. Ltd.), polybutene (HV-100F, manufactured by Nippon Oil Co. Ltd.) and di-iostearyl malate (Cosmol 222, manufactured by Nissin Oil Mills Ltd.) were solidified by compounding 20% of ceresine or candelira wax.

Each of the solidified product was coated on paraffin paper and gloss was measured with a handy glossmeter manufactured by HORIBA Ltd. Gloss was expressed by intensity of light reflected on the coated surface of paraffin paper at incident angle/reflection angle of 60°.

TABLE

| Ester | Gloss | |
|---|---|---|
| | Ceresin | Candelira wax |
| DD-DA/1:0.5 | 60 | 61 |
| DD-DA/1:0.7 | 59 | 61 |
| DD-HDA/1:0.5 | 63 | 61 |
| DD-HDA/1:0.7 | 64 | 61 |
| DD-HDAS/1:0.7 | 63 | 61 |
| DD-SEBA/1:0.5 | 63 | 58 |
| DD-SEBA/1:0.7 | 64 | 57 |
| DD-SEBAS/1:0.7 | 64 | 58 |
| liquid lanolin | 66 | 64 |
| polybutene | 45 | 48 |
| di-iostearyl malate | 35 | 41 |

The results indicate that gloss of any of the tested esters of the present invention are almost the same as gloss of liquid lanolin, and much higher than gloss of polybutene and di-iostearyl malate.

Example 36

According to the composition shown in the following Table and according to the following manner, an ointment was prepared.

Liquid paraffin, DD-DA/1:0.5 obtained in Example 28, dimethyl siloxane and cetostearyl alcohol were heated up to 70° C. and mixed until a uniform mixture was obtained (oil phase).

Cetrimide and chlorocresol were dissolved in purified water at 70° C. To the aqueous solution thus obtained, the oil phase obtained above was added with stirring to make a uniform mixture, which was then cooled to room temperature to obtain an ointment.

TABLE

| Ingredient | Composition % by weight |
|---|---|
| liquid paraffin | 30.0 |
| DD-DA/1:0.5 | 10.0 |
| dimethyl siloxane | 10.0 |
| cetostearyl alcohol | 5.0 |
| cetrimide | 0.5 |
| chlorocresol | 0.1 |
| purified water | balance |

Example 37

According to the same manner as in Example 36 except that DD-DA/1:0.5 was replaced with DD-SEBA/1:0.5 obtained in Example 33, an ointment was prepared.

Comparative Example 7

According to the same manner as in Example 36 except that DD-DA/1:0.5 was replaced with glyceride tristearate, an ointment was prepared.

Example 38

According to the composition shown in the following Table and according to the following manner, an emollient cream was prepared.

Dipropylene glycol, glycerin and triethanolamine were dissolved in purified water, and heated up to 70° C. (water phase). Other ingredients were mixed and fused at 70° C. (oil phase). To the water phase, the oil phase was added slowly with stirring. After stirring further, the obtained mixture was emulsified with an emulsifier and cooled to room temperature to obtain an emollient cream.

TABLE

| Ingredient | Composition % by weight |
|---|---|
| DD-HDA/1:0.5 obtained in Example 30 | 3.0 |
| Sorbitan monostearate | 3.0 |
| stearic acid | 3.0 |
| vaseline | 6.0 |
| cetyl alcohol | 5.0 |
| POE(20)-cetyl alcohol ether | 2.0 |
| propylene glycol monostearate | 3.0 |
| dipropylene glycol | 3.0 |
| glycerine | 3.0 |
| triethanolamine | 1.0 |
| antiseptic, antioxidant | q.s. |
| purified water | balance |

Example 39

According to the same manner as in Example 38 except that DD-HDA/1:0.5 was replaced with DD-SEBA/1:0.5 obtained in Example 33, an emollient cream was prepared.

Comparative Example 8

According to the same manner as in Example 38 except that DD-HDA/1:0.5 was replaced with glyceryl tri-2-ethylhexanate, an emollient cream was prepared.

Example 40

According to the composition shown in the following Table and according to the following manner, a milky lotion was prepared.

Polyethylene glycol 1500, 1,3-butyleneglycol and triethanolamine were added to purified water, and dissolved by heating up to 70° C. (water phase). Other ingredients were mixed and fused at 70° C. (oil phase). To the water phase, the oil phase was added slowly with stirring for pre-emulsification. The resulting mixture was further emulsified uniformly with an emulsifier and cooled to room temperature to obtain a milky lotion.

TABLE

| Ingredient | Composition % by weight |
|---|---|
| DD-HDA/1:0.5 obtained in Example 30 | 3.0 |
| stearic acid | 2.0 |
| vaseline | 3.0 |
| cetyl alcohol | 1.0 |
| sorbitan monooleate | 2.0 |
| polyethylene glycol 1500 | 3.0 |
| 1,3-butylene glycol | 5.0 |
| triethanolamine | 1.0 |
| perfume, preservative | q.s. |
| purified water | balance |

Example 41

According to the same manner as in Example 40 except that DD-HDA/1:0.5 was replaced with DD-SEBA/1:0.5 obtained in Example 33, a milky lotion was prepared.

Comparative Example 9

According to the same manner as in Example 40 except that DD-HDA/1:0.5 was replaced with glyceryl tri-2-ethylhexanate, a milky lotion was prepared.

Example 42

According to the composition shown in the following Table and according to the following manner, a liquid cream shampoo was prepared.

After purified water was heated up to 70° C., other ingredients were added thereto and dissolved uniformly. Then, the resulting mixture was cooled to obtain a liquid cream shampoo.

| Ingredient | Composition % by weight |
|---|---|
| DD-HDA/1:0.5 obtained in Example 30 | 2.0 |
| sodium polyoxyethylene(3) lauryl sulfate(30%) | 30.0 |
| sodium laurylsulfate(30%) | 15.0 |
| lauric diethanolamide | 3.0 |
| polyethyleneglycol distearate | 2.0 |
| perfume, preservative | q.s. |
| sequestering agent and pH adjusting agent | q.s. |
| purified water balance | balance |

Example 43

According to the same manner as in Example 42 except that DD-HDA/1:0.5 was replaced with DD-SEBA/1:0.5 obtained in Example 33, a liquid cream shampoo was prepared.

Comparative Example 10

According to the same manner as in Example 42 except that DD-HDA/1:0.5 was replaced with cetyl 2-ethylhexanate, a liquid cream shampoo was prepared.

Example 44

According to the composition shown in the following Table and according to the following manner, a hair conditioner was prepared.

Stearyl trimethylammonium chloride and presevative were dissolved in purified water by heating up to 70° C. to obtain an aqueous solution.

DD-HDA/1:0.7 obtained in Example 31, glyceryl monostearate, cetyl alcohol, glycerin and perfume were mixed at 70° C. with stirring. The mixture was added to the aqueous solution obtained above, and mixed thoroughly with stirring, followed by cooling to prepare a hair conditioner.

| Ingredient | Composition % by weight |
|---|---|
| DD-HDA/1:0.7 obtained in Example 31 | 2.0 |
| stearyl trimethylammonium chloride | 3.0 |
| glyceryl monostearate | 0.5 |
| cetyl alcohol | 3.0 |
| glycerin | 3.0 |
| perfume, preservative | q.s. |
| purified water | balance |

Example 45

According to the same manner as in Example 44 except that DD-HDA/1:0.7 was replaced with DD-SEBA/1:0.7 obtained in Example 34, a hair conditioner was prepared.

Comparative Example 11

According to the same manner as in Example 44 except that DD-HDA/1:0.5 was replaced with beef tallow fatty acid glyceride, a hair conditioner was prepared.

Example 46

Using DD-HDA/1:0.5 obtained in Example 30 and according to the composition shown in the following Table, a rinse was prepared.

| Ingredient | Composition % by weight |
|---|---|
| silicone oil | 3.0 |
| liquid paraffin | 1.0 |
| DD-HDA/1:0.5 obtained in Example 30 | 1.0 |
| cetyl alcohol | 1.5 |
| stearyl alcohol | 1.0 |
| stearyl trimethylammonium chloride | 3.0 |
| glycerin | 3.0 |
| perfume | q.s. |
| coloring agent | q.s. |
| preservative | q.s. |
| purified water | balance |

Example 47

According to the same manner as in Example 46 except that DD-HDA/1:0.5 was replaced with DD-SEBA/1:0.5 obtained in Example 33, a rinse was prepared.

Comparative Example 12

According to the same manner as in Example 46 except that DD-HDA/1:0.5 was replaced with di-isostearyl malate, a rinse was prepared.

Example 48

Titanium dioxide, Red No. 201 and Red No. 202 were added to a portion of DD-DA/1:0.7 obtained in Example 29. The mixture was kneaded with a roller and mixed uniformly (pigment portion).

Red No. 223 was dissolved in the remaining DD-DA/1:0.7 obtained in Example 29 (dye portion). Other ingredients were mixed and fused by heating, and, thereto the pigment portion and dye portion were added and dispersed uniformly by a homomixer. Then, the dispersion was put in a mold and cooled rapidly to make a stick.

TABLE

| Ingredient | Composition % by weight |
|---|---|
| DD-DA/1:0.7 obtained in Example 29 | 30.0 |
| diglyceryl triisostearyate | 14.0 |
| trimethylol propane triisostearate | 16.0 |
| beewax | 9.0 |
| lanolin | 6.0 |
| carnauba wax | 7.0 |
| ceresine | 6.0 |
| hard lanolin fatty acid cholesteryl ester | 5.0 |
| titanium dioxide | 5.0 |
| Red No.201 | 0.6 |
| Red No.202 | 1.2 |
| Red No.223 | 0.2 |
| perfume, preservative | q.s. |

Example 49

According to the same manner as in Example 48 except that DD-DA/1:0.7 was replaced with DD-SEBA 1:0.7 obtained in Example 34, a lipstick was prepared.

Comparative Example 13

According to the same manner as in Example 48 except that DD-DA/1:0.7 was replaced with di-isostearyl malic acid (Cosmol 222, manufactured by Nissin Oil Mills Ltd.), a lipstick was prepared.

Example 50

According to the same manner as in Example 48 except that DD-DA/1:0.7 was replaced with DD-HDA/1:0.7 obtained in Example 31, a lipstick was prepared.

Example 51

According to the same manner as in Example 50 except that DD-HDA/1:0.7 was replaced with DD-SEBAS/1:0.7 obtained in Example 35, a lipstick was prepared.

Comparative Example 14

According to the same manner as in Example 50 except that DD-HDA/1:0.7 was replaced with polybutene (PARLEAM 18, manufactured by NOF CORP.), a lipstick was prepared.

Example 52

Lipgloss

| No. | Ingredient | Composition % by weight |
|---|---|---|
| 1. | dextrin palmitate | 10.0 |
| 2. | DD-HDAS/1:0.7 obtained in Example 32 | 30.0 |
| 3. | macadamia nut oil fatty acid cholesteryl ester | 10.0 |
| 4. | methyl phenyl polysiloxane | 30.0 |
| 5. | glyceryl tri-2-ethyl hexanate | 5.0 |
| 6. | liquid paraffin | 15.0 |

Whole ingredients were heated, fused and mixed. Then, the mixture was poured in a vessel, then, cooled and solidified to obtain aimed lipgloss.

Example 53

According to the same manner as in Example 52 except that DD-HDAS/1:0.7 was replaced with DD-SEBAS/1:0.7 obtained in Example 35, a lipgloss was prepared.

Comparative Example 15

According to the same manner as in Example 52 except that DD-HDAS/1:0.7 was replaced with polybutene (PARLEAM 18, manufactured by NOF CORP.), a lipgloss was prepared.

Example 54 Powdery Foundation

| No. | Ingredient | Composition % by weight |
|---|---|---|
| 1. | talc | 15.0 |
| 2. | mica | 30.0 |
| 3. | kaolin | 15.0 |
| 4. | titanium dioxide | 15.0 |
| 5. | titanated mica | 3.0 |
| 6. | zinc stearate | 1.0 |
| 7. | nylon powder | 5.0 |
| 8. | red iron oxide | 1.0 |
| 9. | yellow iron oxide | 3.0 |
| 10. | black iron oxide | 0.2 |
| 11. | squalane | 6.0 |
| 12. | DD-DA/1:0.7 obtained in Example 29 | 1.0 |
| 13. | octyldodecyl myristate | 2.0 |
| 14. | neopentylglycol diisooctanate | 2.0 |
| 15. | sorbitan monooleate | 0.5 |
| 16. | preservative | q.s. |
| 17. | antioxidant | q.s. |
| 18. | perfume | q.s. |

Above ingredients No. 1 and No. 8-10 were mixed with henshel type mixer. Then, ingredients 2-7 were added thereto and mixed thoroughly. The resulting mixture and a mixture which was prepared by mixing ingredients 12-18 with heating to 70° C. and fusing were mixed and crushed to obtain aimed powdery foundation.

Example 55

According to the same manner as in Example 54 except that DD-DA/1:0.7 was replaced with DD-SEBA/1:0.7 obtained in Example 34, a powdery foundation was prepared.

Comparative Example 16

According to the same manner as in Example 54 except that DD-DA/1:0.7 was replaced with diisostearyl malate, a powdery foundation was prepared.

Example 56 Milky Foundation

| No. | Ingredient | Composition % by weight |
|---|---|---|
| 1. | ion-exchanged water | 60.9 |
| 2. | dispersant | 0.1 |
| 3. | propylene glycol | 5.0 |

-continued

| No. | Ingredient | Composition % by weight |
|---|---|---|
| 4. | preservative | q.s. |
| 5. | polyoxyethylene modified dimethylpolysiloxane | 4.0 |
| 6. | decamethylcyclopentasiloxane | 12.0 |
| 7. | DD-HDA/1:0.7 obtained in Example 34 | 5.0 |
| 8. | zinc white | 10.0 |
| 9. | sericite | 0.36 |
| 10. | titanium dioxide | 8.32 |
| 11. | yellow iron oxide | 0.80 |
| 12. | red iron oxide | 0.36 |
| 13. | black iron oxide | 0.16 |
| 14. | perfume | q.s. |

Above ingredients No. 1-4 were mixed with heating, and, thereto, ingredients No. 9-13 were added and dispersed. Then, the resulting was heated to 70° C. and mixed with ingredients 5-7, followed by carrying out emulsification. Then, the emulsified mixture was cooled to room temperature and, thereto, ingredient 14 was added to obtain aimed milky foundation.

Example 57

According to the same manner as in Example 56 except that DD-HDA/1:0.7 was replaced with DD-SEBA/1:0.7 obtained in Example 34, a milky foundation was prepared.

Comparative Example 17

According to the same manner as in Example 56 except that DD-HDA/1:0.7 was replaced with diisostearyl malate, a milky foundation was prepared.

Example 58 Foundation

| No. | Ingredient | Composition % by weight |
|---|---|---|
| 1. | silicon treated talc | 19.0 |
| 2. | silicon treated mica | 40.0 |
| 3. | silicon treated titanium dioxide | 5.0 |
| 4. | zinc white | 15.0 |
| 5. | silicon treated red iron oxide | 1.0 |
| 6. | silicon treated yellow iron oxide | 3.0 |
| 7. | silicon treated black iron oxide | 0.2 |
| 8. | zinc stearate | 0.1 |
| 9. | nylon powder | 2.0 |
| 10. | DD-DA/1:0.5 obtained in Example 28 | 4.0 |
| 11. | solid paraffin | 0.5 |
| 12. | dimethyl polysiloxane | 4.0 |
| 13. | glyceryl triisooctanate | 5.0 |
| 14. | octylmethoxy cinnamte | 1.0 |
| 15. | preservative | q.s. |
| 16. | antioxidant | q.s. |
| 17. | perfume | q.s. |

Above ingredients No. 1-9 were mixed with henshel type mixer. Then, the resulting mixture and a mixture which was prepared by mixing ingredients 10-17 with heating to 70° C. and fusing were mixed and crushed to obtain aimed foundation.

Example 59

According to the same manner as in Example 58 except that DD-DA/1:0.5 was replaced with DD-SEBA/1:0.5 obtained in Example 33, a foundation was prepared.

Comparative Example 18

According to the same manner as in Example 56 except that DD-DA/1:0.5 was replaced with diisostearyl malate, a foundation was prepared.

Example 60 Oily Stick Foundation

| No. | Ingredient | Composition % by weight |
|---|---|---|
| 1. | talc | 15.0 |
| 2. | titanium oxide | 7.0 |
| 3. | kaolin | 20.0 |
| 4. | mica | 3.3 |
| 5. | red iron oxide . | 1.0 |
| 6. | yellow iron oxide | 3.0 |
| 7. | black iron oxide | 0.2 |
| 8. | solid paraffin | 3.0 |
| 9. | micro crystaline wax | 7.0 |
| 10. | vaseline | 15.0 |
| 11. | dimethyl polysiloxane | 3.0 |
| 12. | DD-HDAS/1:0.7 obtained in Example 32 | 5.0 |
| 13. | isopropyl palmitate | 17.0 |
| 14. | antioxidant | q.s. |
| 15. | perfume | q.s. |

Above ingredients No. 8-14 were mixed and fused at 85° C., and ingredients No. 1-7 were added thereto, mixed by a disper and dispersed with a colloid mill. Ingredient 15 was added to the resulting mixture, and, after being de-gassed, the mixture was poured to a vessel at 70° C. and cooled.

Example 61

According to the same manner as in Example 60 except that DD-HDAS/1:0.7 was replaced with DD-SEBAS/1:0.7 obtained in Example 35, an oily stick foundation was prepared.

Comparative Example 19

According to the same manner as in Example 56 except that DD-HDAS/1:0.7 was replaced with polybutene (PARLEAM 18, manufactured by NOF CORP.) an oily stick foundation was prepared.

Example 62 Sunscreen Agent

| No. | Ingredient | Composition % by weight |
|---|---|---|
| 1. | ultra fine particle titanium oxide | 5.0 |
| 2. | ion-exchanged water | 54.95 |
| 3. | 1,3-butylene glycol | 7.0 |
| 4. | EDTA-2Na | 0.05 |
| 5. | triethanolamine | 1.0 |
| 6. | oxybenzone | 2.0 |
| 7. | octyl paramethoxycinnamete | 5.0 |
| 8. | squalane | 10.0 |
| 9. | DD-HDA/1:0.5 obtained in Example 30 | 5.0 |
| 10. | stearyl alcohol | 3.0 |
| 11. | stearic acid | 3.0 |
| 12. | glyceryl monostearate | 3.0 |
| 13. | ethyl polyacrylate | 1.0 |
| 14. | preservative | q.s. |
| 15. | antioxidant | q.s. |
| 16. | perfume | q.s. |

Above ingredients No. 2-5 were mixed and fused at 70° C., and ingredients No. 1 was added thereto and dispersed thoroughly. Then, the resulting mixture and a mixture which was prepared by mixing ingredients 6-16 with heating and fusing were mixed and emulsified with a homogenizer. Thereafter, the resulting was cooled with stirring to obtain aimed sunscreen agent.

Example 63

According to the same manner as in Example 62 except that DD-HDA/1:0.5 was replaced with DD-SEBA/1:0.5 obtained in Example 33, a sunscreen agent was prepared.

Comparative Example 20

According to the same manner as in Example 62 except that DD-HDA/1:0.5 was replaced with polybutene (PARLEAM 18, manufactured by NOF CORP.), a sunscreen agent was prepared.

Example 64 Mascara

| No. | Ingredient | Composition % by weight |
|---|---|---|
| 1. | black iron oxide | 10.0 |
| 2. | DD-DA/1:0.7 obtained in Example 29 | 20.0 |
| 3. | polyacrylic acid ester emulsion | 20.0 |
| 4. | solid paraffin | 8.0 |
| 5. | lanolin wax | 8.0 |
| 6. | light isoparaffin | 17.0 |
| 7. | sorbitan sesquioleate | 3.0 |
| 8. | purified water | 10.0 |
| 9. | 2-ethylhexyl-p-cinnamate | 3.0 |
| 10. | preservative | q.s. |
| 11. | perfume | q.s. |

Oily ingredients No. 2-7, 9, 10 and 11 were mixed with heating and fusing. (oil part) To the oil part, ingredient 1 was added and dispersion treatment was conducted. Then, heated ingredient 8 was added to the oil part, and further dispersion treatment, then cooling, were conducted to obtain aimed mascara.

Example 65

According to the same manner as in Example 64 except that DD-DA/1:0.7 was replaced with DD-SEBA/1:0.7 obtained in Example 34, a mascara was prepared.

Comparative Example 21

According to the same manner as in Example 64 except that DD-DA/1:0.7 was replaced with polybutene (PARLEAM 18, manufactured by NOF CORP.), a mascara was prepared.

Example 66 Milky Eye Shadow

| No. | Ingredient | Composition % by weight |
|---|---|---|
| 1. | talc | 10.0 |
| 2. | kaolin | 4.0 |
| 3. | pigment | 5.0 |
| 4. | DD-DA/1:0.5 obtained in Example 28 | 20.0 |

-continued

| No. | Ingredient | Composition % by weight |
|---|---|---|
| 5. | stearic acid | 7.0 |
| 6. | isopropyl myristate | 1.0 |
| 7. | liquid paraffin | 4.0 |
| 8. | propylene glycol monolaurate | 1.5 |
| 9. | antioxidant | q.s. |
| 10. | perfume | q.s. |
| 11. | purified water | 45.0 |
| 12. | butylene glycol | 5.0 |
| 14. | light isoparaffin | 1.0 |
| 15. | 2-ethylhexyl-p-cinnamate | 5.0 |
| 16. | preservative | q.s. |
| 17. | triethanol amine | 1.0 |
| 18. | sequestering agent | q.s. |

Above ingredients No. 4-8 and 15 were mixed with heating to 70° C. and fusing, and ingredients No. 13 and 14 were added thereto. (oil part)

Ingredients 12, 16 and 17 were dissolved in ingredient 11, and ingredients 1, 2 and 3 were added thereto, thoroughly dispersed and heated to 70-80° C. (water part)

Then, the water part was added to the oil part and emulsified. Using an emulsifier, emulsified particles were adjusted, and cooling and de-gassing were conducted to obtain aimed milky eye shadow.

Example 67

According to the same manner as in Example 66 except that DD-DA/1:0.5 was replaced with DD-SEBA/1:0.5 obtained in Example 33, a milky eye shadow was prepared.

Comparative Example 22

According to the same manner as in Example 66 except that DD-DA/1:0.5 was replaced with polybutene (PARLEAM 18, manufactured by NOF CORP.), a milky eye shadow was prepared.

Reference Example 12

Stability at 40° C. of the ointment, lip stick, emollient cream, shampoo, rinse, hair conditioner, milky lotion, powdery foundation, milky foundation, dual-use-foundation, oily stick foundation, sunscreen agent, mascara, milky eye shadow and lipgloss prepared in Examples 36-67 and those prepared in Comparative examples 7-22 were evaluated. The results according to the following criteria are shown in the following Table.

TABLE

| Tested Sample | stability |
|---|---|
| ointment of Example 36 | ◯ |
| ointment of Example 37 | ◯ |
| emollient cream of Example 38 | ◯ |
| emollient cream of Example 39 | ◯ |
| milky lotion of Example 40 | ◯ |
| milky lotion of Example 41 | ◯ |
| liquid creamshampoo of Example 42 | ◯ |
| liquid creamshampoo of Example 43 | ◯ |
| hair conditioner of Example 44 | ◯ |
| hair conditioner of Example 45 | ◯ |
| rinse of Example 46 | ◯ |
| rinse of Example 47 | ◯ |
| lipstick of Example 48 | ◯ |

TABLE-continued

| Tested Sample | stability |
|---|---|
| lipstick of Example 49 | ○ |
| lipstick of Example 50 | ○ |
| lipstick of Example 51 | ○ |
| lipgloss of Example 52 | ○ |
| lipgloss of Example 53 | ○ |
| powdery foundation of Example 54 | ○ |
| powdery foundation of Example 55 | ○ |
| milky foundation of Example 56 | ○ |
| milky foundation of Example 57 | ○ |
| dual-use foundation of Example 58 | ○ |
| dual-use foundation of Example 59 | ○ |
| oily stick foundation of Example 60 | ○ |
| oily stick foundation of Example 61 | ○ |
| sunscreen agent of Example 62 | ○ |
| sunscreen agent of Example 63 | ○ |
| mascara of Example 64 | ○ |
| mascara of Example 65 | ○ |
| milky eye shadow of Example 66 | ○ |
| milky eye shadow of Example 67 | ○ |
| ointment of CP Example 7 | ○ |
| (hereinafter CP Example indicates Comparative Example) | |
| emollient cream of CP Example 8 | ○ |
| milky lotion of CP Example 9 | Δ |
| liquid creamshampoo of CP Example 10 | ○ |
| hair conditioner of CP Example 11 | Δ |
| rinse of CP Example 12 | Δ |
| lipstick of CP Example 13 | ○ |
| lipstick of CP Example 14 | ○ |
| lipgloss of CP Example 15 | ○ |
| powdery foundation of CP Example 16 | ○ |
| milky foundation of CP Example 17 | ○ |
| dual-use foundation of CP Example 18 | ○ |
| oily stick foundation of CP Example 19 | ○ |
| sunscreen agent of CP Example 20 | Δ |
| mascara of CP Example 21 | ○ |
| milky eye shadow of CP Example 22 | ○ |

"○": Stable even after 30 days from preparation.
"Δ": Phase separation or deposition was observed on 10-29 days after preparation.
"X": Phase separation or deposition was observed within 10 days The results show that stability of the milky lotion, hair conditioner, rinse and sunscreen agent prepared in Examples are better than those prepared in Comparative examples.

Reference Example 13

Female panelists were requested to use-test the ointments prepared in Examples 36 and 37 and Comparative example 7, the emollient creams prepared in Examples 38 and 39 and Comparative example 8 and the milky lotions prepared in Examples 40 and 41 and Comparative example 9. The results according to the following criteria are shown in the following table.

TABLE

| | Feeling of use | | | Durability | | |
|---|---|---|---|---|---|---|
| | Non-sticky feel | dry feeling | smooth feel | Non-sticky feel | dry feeling | smooth feel |
| ointment of Example 36 | ◎ | ○ | ◎ | ◎ | ○ | ◎ |
| ointment of Example 37 | ◎ | ○ | ◎ | ○ | ○ | ◎ |
| emollient cream of Example 38 | ◎ | ○ | ○ | ◎ | ○ | ◎ |
| emollient cream of Example 39 | ○ | ○ | ◎ | ○ | ○ | ◎ |
| milky lotion of Example 40 | ◎ | ◎ | ◎ | ◎ | ◎ | ◎ |
| milky lotion of Example 41 | ○ | ○ | ◎ | ○ | ○ | ◎ |
| ointment of CP example 7 | ○ | ○ | ○ | ○ | ○ | ○ |
| emollient cream of CP example 8 | ○ | Δ | Δ | ○ | Δ | Δ |
| milky lotion of CP example 9 | ○ | Δ | Δ | ○ | Δ | Δ |

[Feeling of use]
"◎": excellent
"○": good
"Δ": insufficient
"X": bad
[Durability]: Feeling of use after used for 5 hours
"◎": excellent
"○": good
"Δ": insufficient
"X": bad The results show that Feeling of use and Durability of the ointments, emollient creams and milky lotions of the present invention are excellent.

Reference Example 14

Female panelists were requested to use-test the shampoos prepared in Example 42 and 43 and Comparative example 10, the hair conditioners prepared in Examples 44 and 45 and Comparative example 11 and rinses prepared in Examples 46 and 46 and Comparative example 12. Sensory evaluations were conducted about moist feel, softness, gloss and manageability of hair. The results according to the following criteria are shown in the following table.

TABLE

| | Moist feel | Softness | gloss | manageability |
|---|---|---|---|---|
| shampoo of Example 42 | ○ | ◎ | ◎ | ○ |
| shampoo of Example 43 | ○ | ○ | ○ | Δ |
| hair conditioner of Example 44 | ○ | ◎ | ◎ | ○ |
| hair conditioner of Example 45 | ○ | ○ | ◎ | ○ |
| rinse of Example 46 | ○ | ◎ | ◎ | ○ |
| rinse of Example 47 | ○ | ○ | ○ | ○ |
| shampoo of CP example 10 | ○ | ○ | Δ | Δ |
| hair conditioner of CP example 11 | Δ | ○ | Δ | ○ |
| rinse of CP example 12 | Δ | Δ | ○ | Δ |

[Moist feel]
"◎": excellent
"○": good
"Δ": fair
"X": not moist
[Softness]
"◎": very soft
"○": soft
"Δ": middle of soft and hard
"X": hard
[gloss]

TABLE-continued

|  | Moist feel | Softness | gloss | manageability |
|---|---|---|---|---|

"◯": very glossy
"◯": glossy
"Δ": little glossy
"X": not glossy
[manageability]
"◯": excellent
"◯": good
"Δ": fair
"X": bad The results show that feeling of use of the shampoo, hair conditioner and rinse of the present invention are excellent.

Reference Example 15

Female panelists were requested to use-test the lipsticks prepared in Examples 48-51 and Comparative example 13-14 and the lipgloss prepared in Examples 52 and 53 and Comparative example 15. Sensory evaluations were conducted about moist feel, adhesiveness, spreadability, gloss, oxidation stability and perspiration. The results according to the following criteria are shown in the following table.

TABLE

|  | Feeling of use | | | |
|---|---|---|---|---|
|  | moist feel | adhesiveness | spreadability | gloss |
| lipstick of Example 48 | ◯ | ◎ | ◯ | ◎ |
| lipstick of Example 49 | ◯ | ◎ | ◯ | ◎ |
| lipstick of Example 50 | ◯ | ◎ | ◯ | ◎ |
| lipstick of Example 51 | ◯ | ◎ | ◯ | ◎ |
| lipgloss of Example 52 | ◯ | ◎ | ◯ | ◎ |
| lipgloss of Example 53 | ◯ | ◎ | ◯ | ◎ |
| lipstick of CP Example 13 | ◯ | ◯ | ◯ | ◯ |
| lipstick of CP Example 14 | Δ | ◯ | Δ | ◯ |
| lipgloss of CP Example 15 | Δ | ◯ | Δ | ◯ |

|  | oxidation stability | perspiration |
|---|---|---|
| lipstick of Example 48 | ◯ | ◯ |
| lipstick of Example 49 | ◯ | ◯ |
| lipstick of Example 50 | ◯ | ◯ |
| lipstick of Example 51 | ◯ | ◯ |
| lipgloss of Example 52 | ◯ | ◯ |
| lipgloss of Example 53 | ◯ | ◯ |
| lipstick of CP Example 13 | Δ | ◯ |
| lipstick of CP Example 14 | ◯ | Δ |
| lipgloss of CP Example 15 | Δ | Δ |

[Moist feel]
"◎": excellent
"◯": good
"Δ": fair
"X": not moist
[adhesiveness]
"◎": excellent
"◯": good
"Δ": in-between good and bad
"X": bad
[spreadability]
"◎": excellent
"◯": good
"Δ": in-between good and bad
"X": bad
[gloss]
"◎": very glossy
"◯": glossy
"Δ": little glossy
"X": not glossy
[oxidation stability]
Change of odor was evaluated after leaving in an oven at 40° C. for 3 months.
"◯": Almost no change was observed.
"X": A clear change was observed.
[perspiration]
"◯": No perspiration was observed for 2 months or longer.
"Δ": No perspiration was observed for 2 weeks or longer.
"X": Perspiration was observed within 2 weeks.

The results show that the lipstick and lipgloss of the present invention are excellent in feeling of use, oxidation stability and perspiration preventing property.

Reference Example 16

Female panelists were requested to use-test the powdery foundation prepared in Examples 54 and 55 and Comparative example 16, the milky foundation prepared in Examples 56 and 57 and Comparative example 17, the dual-use foundation prepared in Examples 58 and 59 and Comparative example 18, and the oily stick foundation prepared in Examples 60 and 61 and Comparative example 19. Sensory evaluations were conducted about moist feel, adhesiveness, spreadability, smoothness and oxidation stability. The results according to the following criteria are shown in the following table.

TABLE

|  | Feeling of use | | | | |
|---|---|---|---|---|---|
|  | moist feel | adhesiveness | spreadability | gloss | oxidation stability |
| powdery foundation of Example 54 | ◯ | ◎ | ◎ | ◯ | ◎ |
| powdery foundation of Example 55 | ◯ | ◎ | ◎ | ◎ | ◯ |
| milky foundation of Example 56 | ◯ | ◎ | ◯ | ◯ | ◎ |
| milky foundation of Example 57 | ◯ | ◎ | ◯ | ◎ | ◎ |
| dual-use foundation of Example 58 | ◯ | ◎ | ◯ | ◎ | ◎ |
| dual-use foundation of Example 59 | ◯ | ◯ | ◯ | ◎ | ◯ |
| oily stick foundation of Example 60 | ◯ | ◎ | ◎ | ◯ | ◎ |

TABLE-continued

|  | \multicolumn{5}{c}{Feeling of use} |  |  |  |  |
| --- | --- | --- | --- | --- | --- |
|  | moist feel | adhesiveness | spreadability | gloss | oxidation stability |
| oily stick foundation of Example 61 | ○ | ◉ | ◉ | ○ | ○ |
| powdery foundation of CP Example 16 | ○ | ○ | ○ | ○ | ○ |
| milky foundation of CP Example 17 | Δ | ○ | Δ | ○ | ○ |
| dual-use foundation of CP Example 18 | ○ | ○ | ○ | ○ | ○ |
| oily stick foundation of CP Example 19 | Δ | ◉ | ○ | Δ | ◉ |

[Moist feel]
"◉": excellent
"○": good
"Δ": fair
"X": not moist
[adhesiveness]
"◉": excellent
"○": good
"Δ": in-between good and bad
"X": bad
[spreadability]
"◉": excellent
"○": good
"Δ": in-between good and bad
"X": bad
[smoothness]
"◉": very smooth
"○": smooth
"X": not smooth
[oxidation stability]
Change of odor was evaluated after leaving in an oven at 40° C. for 3 months.
"◉": Almost no change was observed.
"○": A little change was observed, but usable level.
"X": A clear change was observed.

The results show that the foundations of the present invention are good in feeling of use and oxidation.

What is claimed is:

1. A cosmetic or an external agent comprising a dimerdiol ester of a monocarboxylic acid having 10 to 32 carbon atoms and/or a dimerdiol ester of a dicarboxylic acid, wherein said dimerdiol is a dimerdiol produced by hydrogenating a dimer acid obtained by dimerization of an unsaturated fatty acid having 11 to 22 carbon atoms.

2. The cosmetic or an external agent according to claim 1, wherein the amount of the dimerdiol ester is 0.1-50% by weight in the cosmetic or external agent.

3. The cosmetic or an external agent according to claim 1, wherein the dimerdiol ester is of a dicarboxylic acid.

4. The cosmetic or an external agent according to claim 3, wherein the dicarboxylic acid comprises an acid represented by the following structural formula 3:

$$HOOC-(CH_2)_n-COOH \quad (3)$$

wherein n is an integer from 1 to 16.

5. The cosmetic or an external agent according to claim 3, wherein the dicarboxylic acid comprises a dimer acid.

6. The cosmetic or an external agent according to claim 3, wherein the dimerdiol ester is obtained by all esterification reaction of a dimerdiol with a dicarboxylic acid wherein the charging ratio is from 0.2 to 1.2 mol in terms of the molar amount of a dicarboxylic acid based on the average molecular weight calculated from its acid value per 1 mol of a dimerdiol based on the average molecular weight calculated from its hydroxyl value.

7. The cosmetic or an external agent according to claim 3, wherein the weight-average molecular weight of the dimerdiol ester is from 4000 to 12000.

8. The cosmetic or an external agent according to claim 1, which further comprises an antioxidant.

9. The cosmetic or an external agent according to claim 8, wherein the antioxidant is vitamin E.

10. A cosmetic or an external agent comprising a dimerdiol ester of a monocarboxylic acid selected from the group consisting of:
    i) linear saturated acids having 4 to 34 carbon atoms,
    ii) branched fatty acids having 4 to 34 carbon atoms,
    iii) linear unsaturated acids having 10 to 32 carbon atoms,
    iv) hydroxy acids having 4 to 34 carbon atoms and
    v) cyclic acids having 4 to 34 carbon atoms, selected from the group consisting of cyclohexanoic acid, hydrogenated rosin, rosin, abietic acid, hydrogenated abietic acid, benzoic acid, p-oxybenzoic acid, p-aminobenzoic acid, salicylic acid, gallic acid, pyrrolidonecarboxylic acid and nicotinic acid; and/or a dimerdiol ester of a dicarboxylic acid, and
    wherein said dimerdiol is a dimerdiol produced by hydrogenating a dimer acid obtained by dimerization of an unsaturated fatty acid having 11 to 22 carbon atoms.

11. The cosmetic or an external agent according to claim 10, wherein the dimerdiol ester is of a monocarboxylic acid having 10 to 32 carbon atoms.

12. The cosmetic or an external agent according to claim 11, wherein the monocarboxylic acid comprises a branched fatty acid.

13. The cosmetic or an external agent according to claim 11, wherein the monocarboxylic acid comprises a linear unsaturated fatty acid having 10 to 32 carbon atoms.

14. The cosmetic or an external agent according to claim 11, wherein the monocarboxylic acid comprises a rosin or a hydrogenated rosin.

* * * * *